United States Patent
Xu

(10) Patent No.: US 11,666,539 B2
(45) Date of Patent: Jun. 6, 2023

(54) SYNTHETIC LIPID-LIKE MATERIALS FOR BRAIN DELIVERY

(71) Applicant: Trustees of Tufts College, Medford, MA (US)

(72) Inventor: Qiaobing Xu, Lexington, MA (US)

(73) Assignee: Trustees of Tufts College, Boston, MA (US)

(*) Notice: Subject to any disclaimer, the term of this patent is extended or adjusted under 35 U.S.C. 154(b) by 0 days.

(21) Appl. No.: 17/339,563

(22) Filed: Jun. 4, 2021

(65) Prior Publication Data

US 2021/0346307 A1    Nov. 11, 2021

Related U.S. Application Data

(63) Continuation of application No. PCT/US2021/030664, filed on May 4, 2021.

(60) Provisional application No. 63/019,530, filed on May 4, 2020.

(51) Int. Cl.
| | |
|---|---|
| *A61K 9/51* | (2006.01) |
| *C07D 209/20* | (2006.01) |
| *C07C 323/58* | (2006.01) |
| *C07C 215/20* | (2006.01) |
| *A61K 45/06* | (2006.01) |
| *C12N 15/113* | (2010.01) |
| *A61K 38/45* | (2006.01) |

(52) U.S. Cl.
CPC ............ *A61K 9/5123* (2013.01); *A61K 38/45* (2013.01); *A61K 45/06* (2013.01); *C07C 215/20* (2013.01); *C07C 323/58* (2013.01); *C07D 209/20* (2013.01); *C12N 15/113* (2013.01); *C12N 2310/11* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 6,852,734 B2 * | 2/2005 | Yamamoto | ............ A61P 43/00 |
| | | | 548/465 |
| 2016/0346208 A1 | 12/2016 | Xu et al. | |
| 2022/0323369 A1 | 10/2022 | Xu | |

FOREIGN PATENT DOCUMENTS

| | | |
|---|---|---|
| WO | WO-2021/022121 A1 | 2/2021 |
| WO | WO-2021/226092 A1 | 11/2021 |

OTHER PUBLICATIONS

Narasimhan et al., Tetrahedron Letters (1966), 6, pp. 603-605.*
Stephens et al., Organic & Biomolecular Chemistry (2016), 14, pp. 6853-6856.*
International Search Report and Written Opinion for International Application No. PCT/US2021/030664 dated Sep. 2, 2021.
Invitation to Pay Additional Fees for International Application No. PCT/US2021/030664 dated Jun. 22, 2021.
PubChem SID 385316719; "[2-1H-indol-3-yl)ethyl]bis(3-methylbutyl)amine," retrieved online <https://pubchem.ncbi.nlm.nih.gov/substance/385316719>: 6 pages (Aug. 30, 2019).
PubChem SID 399019043; "SID 399019043," retrieved online <https://pubchem.ncbi.nlm.nih.gov/substance/399019043>: 5 pages (Dec. 17, 2019).

* cited by examiner

*Primary Examiner* — Brian J Davis
(74) *Attorney, Agent, or Firm* — Foley Hoag LLP; Dana M. Gordon; Alexander J. Chatterley

(57) ABSTRACT

Disclosed are (i) compounds of formula I, or pharmaceutically acceptable salts thereof, and (ii) lipidoid nanoparticles comprising compound of formula I or pharmaceutically acceptable salts thereof, as well as their use as vehicles for drug delivery across the blood-brain barrier.

16 Claims, 27 Drawing Sheets

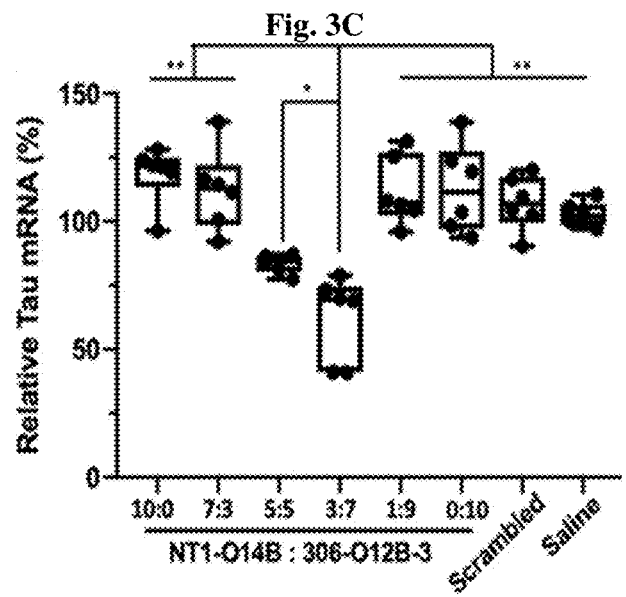
Fig. 3C
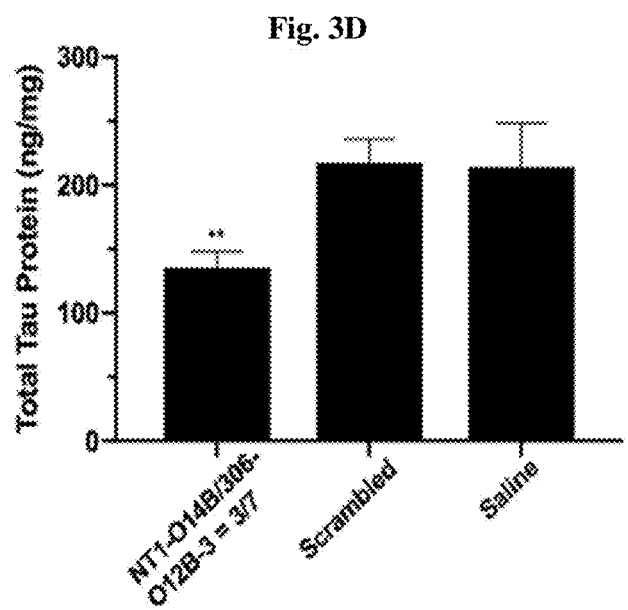
Fig. 3D
Fig. 4A
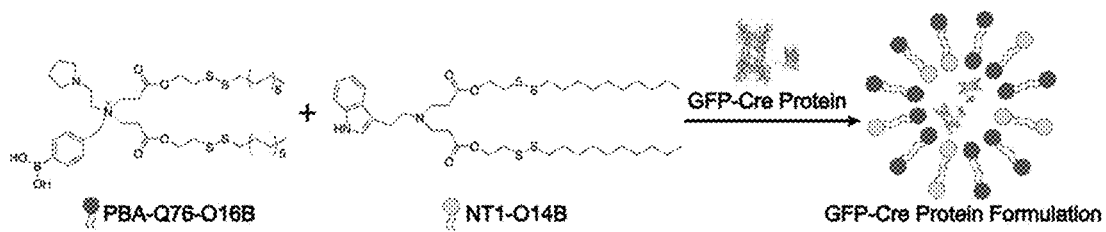

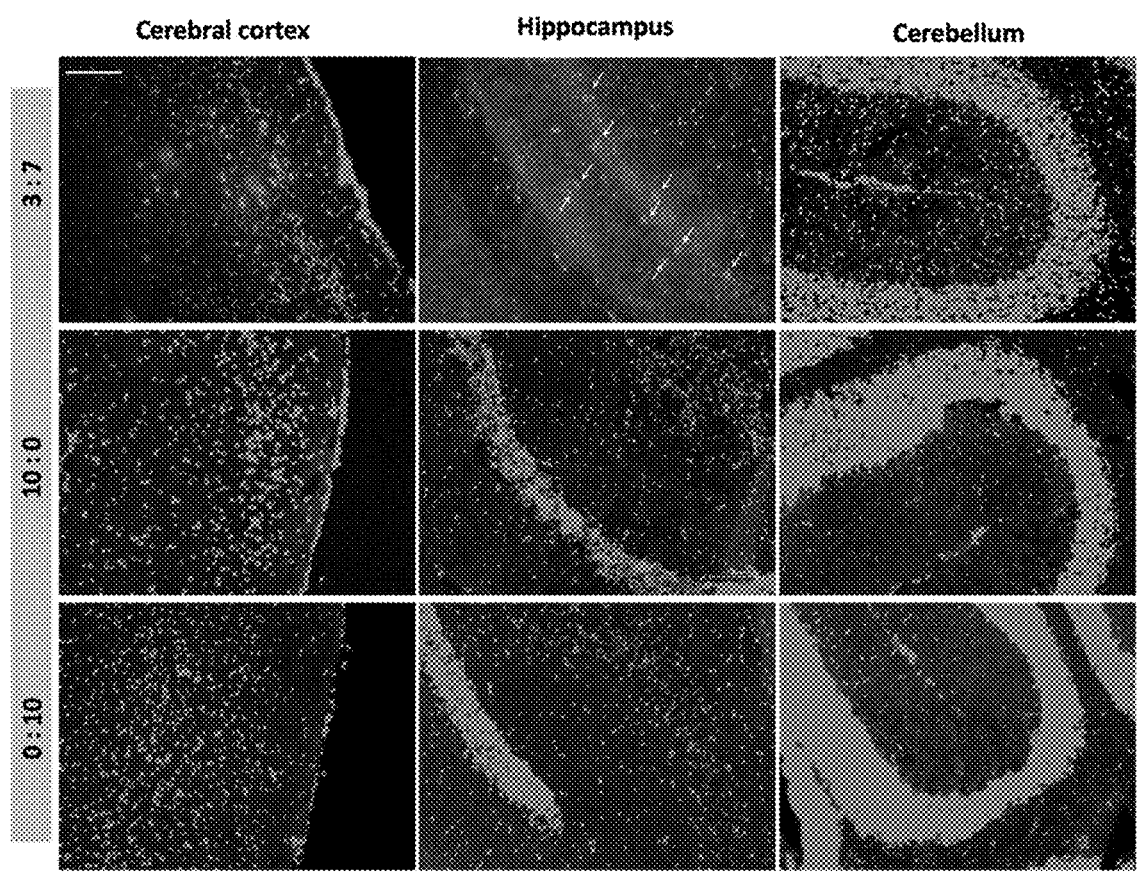

|           | Hydrodynamic size / nm | PDI             | Zeta potential / mv |
|-----------|------------------------|-----------------|---------------------|
| NT1-O12B  | 173.6 ± 1.6            | 0.094 ± 0.007   | 41.6 ± 2.7          |
| NT1-O14B  | 179.2 ± 2.7            | 0.118 ± 0.014   | 39.5 ± 1.8          |
| NT1-O16B  | 166.1 ± 2.3            | 0.102 ± 0.009   | 41.7 ± 1.7          |
| NT1-O18B  | 189.1 ± 1.9            | 0.119 ± 0.012   | 43.1 ± 1.0          |

| | Hydrodynamic size / nm | PDI | Zeta potential / mv | DLC |
|---|---|---|---|---|
| NT1-O18B-AmB | 788.2 ± 10.3 | 0.299 ± 0.012 | -14.64 ± 1.14 | 0.515 |
| NT1-O16B-AmB | 761.8 ± 5.2 | 0.323 ± 0.032 | -13.54 ± 1.06 | 0.530 |
| NT1-O14B-AmB | 791.1 ± 36.8 | 0.316 ± 0.026 | -15.08 ± 1.18 | 0.523 |
| NT1-O12B-AmB | 795.4 ± 11.9 | 0.390 ± 0.029 | -12.93 ± 1.01 | 0.516 |
| NT1-O12B/PBA-Q76O16B-7/3-AmB | 541.0 ± 3.4 | 0.309 ± 0.015 | 19.72 ± 1.54 | 0.483 |
| NT1-O12B/PBA-Q76O16B-5/5-AmB | 297.6 ± 2.9 | 0.295 ± 0.024 | 24.47 ± 0.46 | 0.481 |
| NT1-O12B/PBA-Q76O16B-3/7-AmB | 109.1 ± 1.3 | 0.205 ± 0.015 | 27.64 ± 2.02 | 0.484 |
| NT1-O12B/PBA-Q76O16B-1/9-AmB | 105.4 ± 2.1 | 0.207 ± 0.006 | 32.14 ± 0.55 | 0.487 |
| PBA-Q76O16B-AmB | 98.4 ± 1.4 | 0.189 ± 0.008 | 31.85 ± 3.89 | 0.447 |

| | Hydrodynamic size / nm | PDI | Zeta potential / mv |
|---|---|---|---|
| Blank NT4-O14B/PBA-Q76O16B-3/7 | 95.07 ± 1.24 | 0.099 ± 0.023 | 29.97 ± 2.47 |
| (-30)GFP-Cre loaded NT4-O14B/PBA-Q76O16B-3/7 | 143.65 ± 1.31 | 0.237 ± 0.014 | 15.98 ± 2.63 | ature cited.

SYNTHETIC LIPID-LIKE MATERIALS FOR BRAIN DELIVERY

RELATED APPLICATIONS

This application is a continuation of International Patent Application No. PCT/US2021/030664, filed May 4, 2021; which claims the benefit of priority to U.S. Provisional Application No. 63/019,530, filed May 4, 2020.

GOVERNMENT SUPPORT

This invention was made with government support under grant numbers TR002636 and EB027170 awarded by the National Institutes of Health. The government has certain rights in the invention.

BACKGROUND

The treatment of central nervous systems (CNS) diseases, such as neurodegenerative disorders, brain tumors, brain infections, and stroke, is severely constrained by the blood-brain-barrier (BBB) because it prevents the transfer of most of small molecule drugs and macromolecules (e.g., peptides, gene drugs, and protein drugs) into the brain. To date, extensive efforts have been undertaken to enhance brain delivery efficiency, including direct CNS administration, disruption of the BBB, and carrier vehicle mediated delivery. However, direct administration to the CNS is invasive, which may cause infection and tissue damage, and is also limited by diffusion distance and rapid efflux of drugs out of the CNS within hours. Disruption of the BBB, using techniques such as osmotic disruption, biochemical disruption, and ultrasound-mediated disruption, is effective to introduce drugs into brain, however, these transient BBB openings also allows for the leakage of plasma proteins into the brain, leading to neurotoxicity, vascular pathology, and chronic neuropathologic changes in the brain. Therefore, approaches for safe and efficient delivery of BBB-impermeable cargos, in particular for gene and nucleic acid therapy, into CNS remain to be desired.

The carrier vehicle mediated brain drug delivery is considered a promising and versatile brain delivery system. For decades, various carrier vehicles, such as viral vectors, exosomes, molecular Trojan horses and sundry nanoparticle formulations, have been developed to enhance brain delivery. Viral vectors are effective for gene delivery to brain, but have limitations such as production cost and safety concerns. Exosomes have been utilized to deliver small molecules, proteins and nucleic acids to the brain due to their non-immunogenic nature; however, there still exist many challenges in the isolation methods, cargo loading procedure, in vivo toxicity and pharmacokinetics. The molecular Trojan horse approach, relying on the receptor-specific monoclonal antibodies or peptides to ferry the genetically fused cargo into the brain, is promising in delivery of biologics across the BBB. However, the manufacturing process needs to be tailored specifically for each for different biologic cargo, and the stability, safety and immunogenicity are challenge to clinical development. Crossing the BBB with various nanoparticles, such as liposomes, cationic polymers, inorganic nanoparticles and nanocapsules, have shown promise in delivery of various cargos into the CNS, but complicated modifications are always needed to ensure the particles produced are BBB-permeable.

Neurotransmitters are endogenous chemicals that enable neurotransmission. Notably, some neurotransmitters have been demonstrated to cross the BBB. For example, dimethyltryptamine and other tryptamine derivatives have been shown to cross the BBB by active transport across the endothelial plasma membrane.

SUMMARY

Disclosed herein is a simple, and effective approach for delivering cargos into brain using neurotransmitter-derived synthetic lipids. This approach is very robust, and can be used to successfully deliver different classes of cargos (small molecule, nucleic acid, and protein, etc.) all using the same, simple nanoparticle design.

In one aspect, disclosed are compounds of formula:

$$Y-W-R^{Lipid} \quad (I),$$

or a pharmaceutically acceptable salt thereof, wherein
Y is a moiety derived from a neurotransmitter;
W is $-NR^{20}-$, $-O-$, or $-S-$;
$R^{Lipid}$ is independently substituted or unsubstituted $C_{1-20}$ alkyl, substituted or unsubstituted $C_{1-20}$ alkenyl, substituted or unsubstituted $C_{1-20}$ alkynyl, substituted or unsubstituted $C_{1-20}$ heteroalkyl, substituted or unsubstituted $C_{1-20}$ heteroalkenyl, or substituted or unsubstituted $C_{1-20}$ heteroalkynyl; and
$R^{20}$ is $R^{Lipid}$, H, $C_{1-6}$ alkyl, $C_{1-6}$ alkenyl, or $C_{1-6}$ alkynyl.

In certain aspects, disclosed are lipidoid nanoparticles comprising a compound disclosed herein.

In certain aspects, disclosed are pharmaceutical compositions comprising a lipidoid nanoparticle disclosed herein; and a pharmaceutically acceptable carrier or excipient.

BRIEF DESCRIPTION OF THE DRAWINGS

FIG. 3C is a graph depicting Tau-ASOs formulated with NT1-O14B doped with different ratios of 306-O12B-3, saline, or scrambled Tau-ASO-LNPs were intravenous injected into C57BL/6J mice (n=6 per group) via the tail vein, and the brain was analyzed for total tau mRNA levels. Graphical data are represented as box and whisker plots with individual points overlaid, where error bars represent maximum and minimum values and the boxed line represents the median, *p<0.05 or **p<0.001.

FIG. 3D is graph depicting total tau protein levels of the NT1-O14B/306-O12B-3=3:7 group, comparing to that of saline or scrambled Tau-ASO, **p<0.001. One-way ANOVA, Sidak post hoc analysis.

FIG. 4A is a schematic illustration of mixed LNP formulation using NT1-O14B and PBA-Q76-O16B for GFP-Cre protein delivery into brain.

FIG. 4B are fluorescence images of the brain slices of Ail4 mice treated with (−27)GFP-Cre in different LNP formulations. Ail4 mouse was intravenous injected with (−27)GFP-Cre complexed with NT1-O14B/PBA-Q76-O16B=3:7, 10:0 or 0:10 LNPs. After 3 weeks, the group of NT1-O14B/PBA-Q76-O16B=3:7 showed tdTomato expression indicative of Cre-mediated recombination in cerebral cortex, hippocampus and cerebellum. Scale bar: 100 m.

DETAILED DESCRIPTION

Figure 1A:
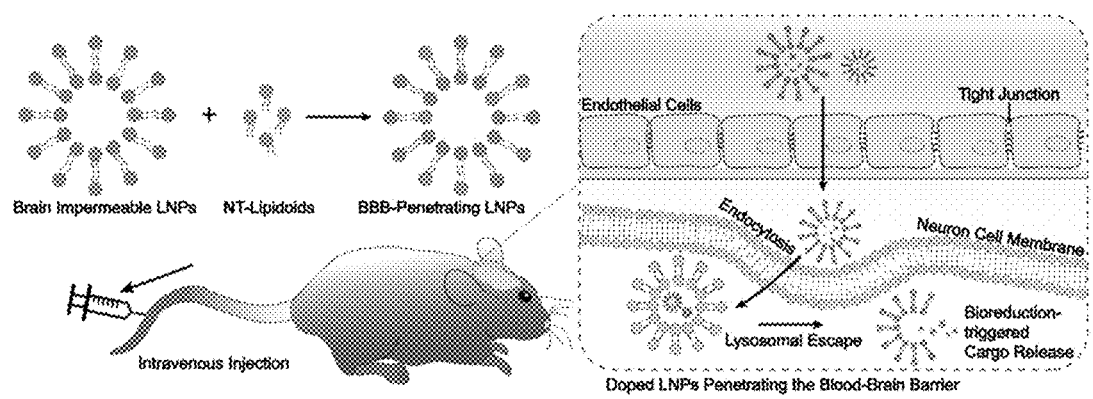
FIG. 1A is a schematic illustration of formulating NT-lipidoid doped LNPs for cargo delivery to brain.

In one aspect, disclosed are compounds of formula I:

$$Y-W-R^{Lipid} \quad (I),$$

or a pharmaceutically acceptable salt thereof, wherein

Y is a moiety derived from a neurotransmitter;

W is $-NR^{20}-$, $-O-$, or $-S-$;

$R^{Lipid}$ is independently substituted or unsubstituted $C_{1-20}$ alkyl, substituted or unsubstituted $C_{1-20}$ alkenyl, substituted or unsubstituted $C_{1-20}$ alknyl, substituted or unsubstituted $C_{1-20}$ heteroalkyl, substituted or unsubstituted $C_{1-20}$ heteroalkenyl, or substituted or unsubstituted $C_{1-20}$ heteroalknyl; and $R^{20}$ is $R^{Lipid}$, H, $C_{1-6}$ alkyl, $C_{1-6}$ alkenyl, or $C_{1-6}$ alkynyl.

In certain embodiments, Y is selected from:

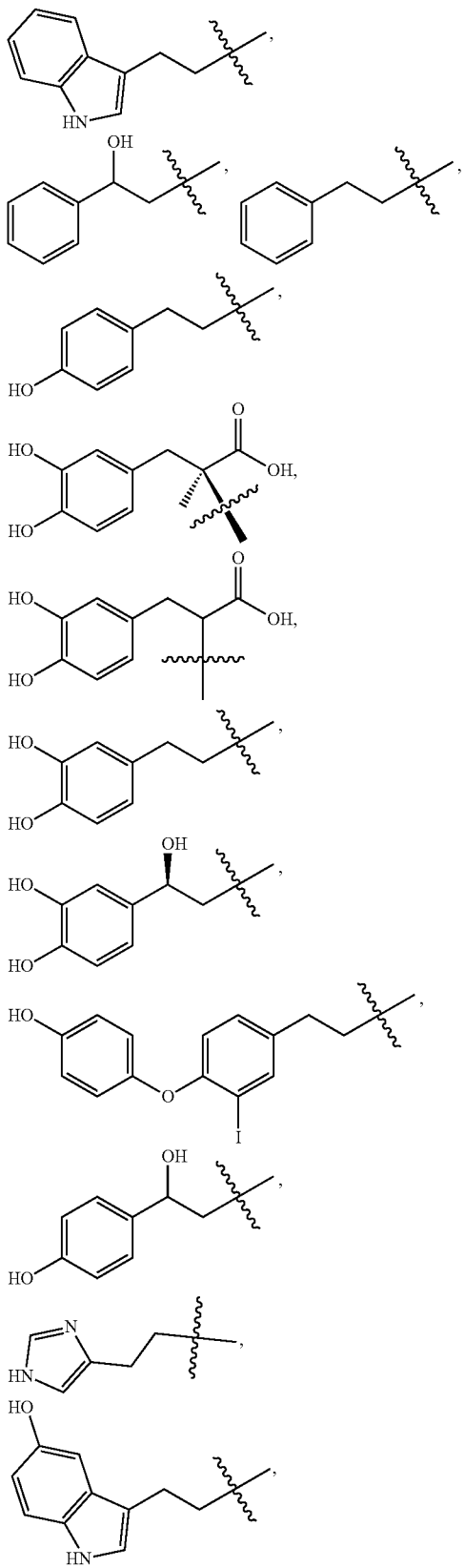

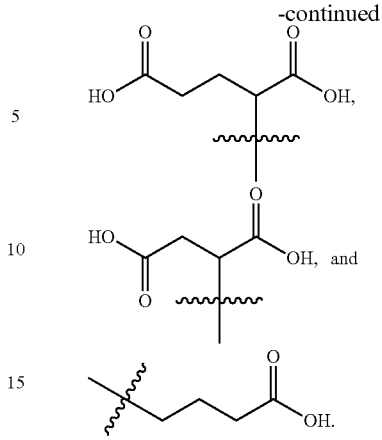

In certain preferred embodiments, Y is

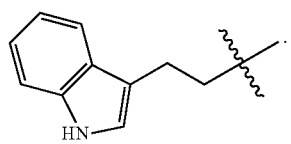 [SMILES: *CCc1c[nH]c2ccccc12]

In certain embodiments, W is —NR$^{20}$— or —S—. In certain embodiments, W is —NR$^{20}$—. In certain embodiments, W is —S—.

In certain embodiments, W is —NR$^{20}$—, and R$^{20}$ is R$^{Lipid}$.

In certain embodiments, W is —NR$^{20}$—, and R$^{20}$ is R$^{Lipid}$ and Y is

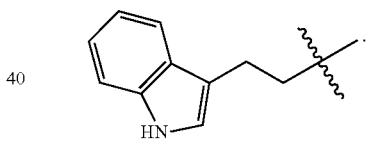

In certain embodiments, R$^{Lipid}$ is of the structure:

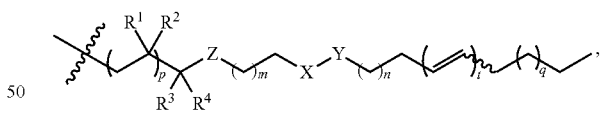

wherein:
each instance of R$^1$ and R$^2$ is independently —H, —OH, —NHR$^{30}$, or —SH;
R$^3$ and R$^4$ are both —H; or R$^3$ and R$^4$ are taken together to form an oxo (=O) group;
Z is —CH$_2$—, —O—, —NR$^{30}$—, or —S—;
X and Y are independently —CH$_2$—, —NR$^{30}$—, —O—, —S—, or —Se—;
m is an integer selected from 1-3;
n is an integer selected from 1-14;
p is 0 or 1;
q is an integer selected from 1-10;
t is 0 or 1; and
R$^{30}$ is —H, $C_{1-6}$ alkyl, $C_{1-6}$ alkenyl, or $C_{1-6}$ alkynyl.

In certain embodiments, each instance of $R^1$ and $R^2$ is independently —H or —OH. In certain embodiments, $R^1$ and $R^2$ are —H. In certain embodiments, $R^1$ is —H; and $R^2$ is —OH.

In certain embodiments, $R^3$ and $R^4$ are —H. In certain embodiments, $R^3$ and $R^4$ are taken together to form an oxo (═O) group.

In certain embodiments, Z is —CH$_2$—, —O—, or —NR$^{30}$—. In certain embodiments, Z is —CH$_2$—.

In certain embodiments, Z is —O—. In certain embodiments, Z is —NR$^{30}$—.

In certain embodiments, $R^1$ and $R^2$ are —H, $R^3$ and $R^4$ are taken together to form an oxo (═O) group, and Z is O.

In certain embodiments, $R^1$ is —H, $R^2$ is —OH, $R^3$ and $R^4$ are —H, and Z is —CH$_2$—.

In certain embodiments, X and Y are independently —CH$_2$— or —O—. In certain embodiments, X and Y are independently —CH$_2$— or —O—, wherein X and Y are not the same. In certain embodiments, X and Y are independently —CH$_2$— or —S—. In certain embodiments, X and Y are both —CH$_2$—. In certain embodiments, X and Y are both —S—.

In certain embodiments, m is 1 or 2. In certain embodiments, m is 1. In certain embodiments, m is 2.

In certain embodiments, n is an integer selected from 4-12. In certain embodiments, n is an integer selected from 6-10.

In certain embodiments, p is 0. In certain embodiments, p is 1.

In certain embodiments, q is an integer selected from 2-8. In certain embodiments, q is an integer selected from 4-8.

In certain embodiments, t is 0. In certain embodiments, t is 1.

In certain embodiments, the compound is selected from the group consisting of:

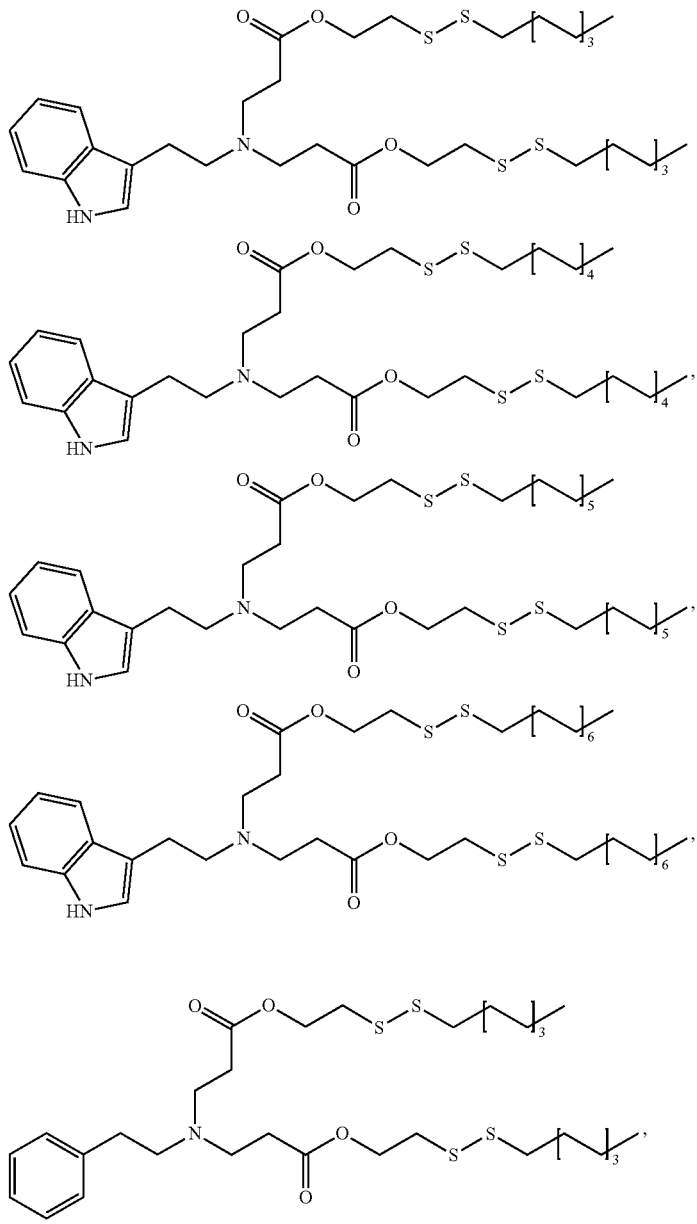

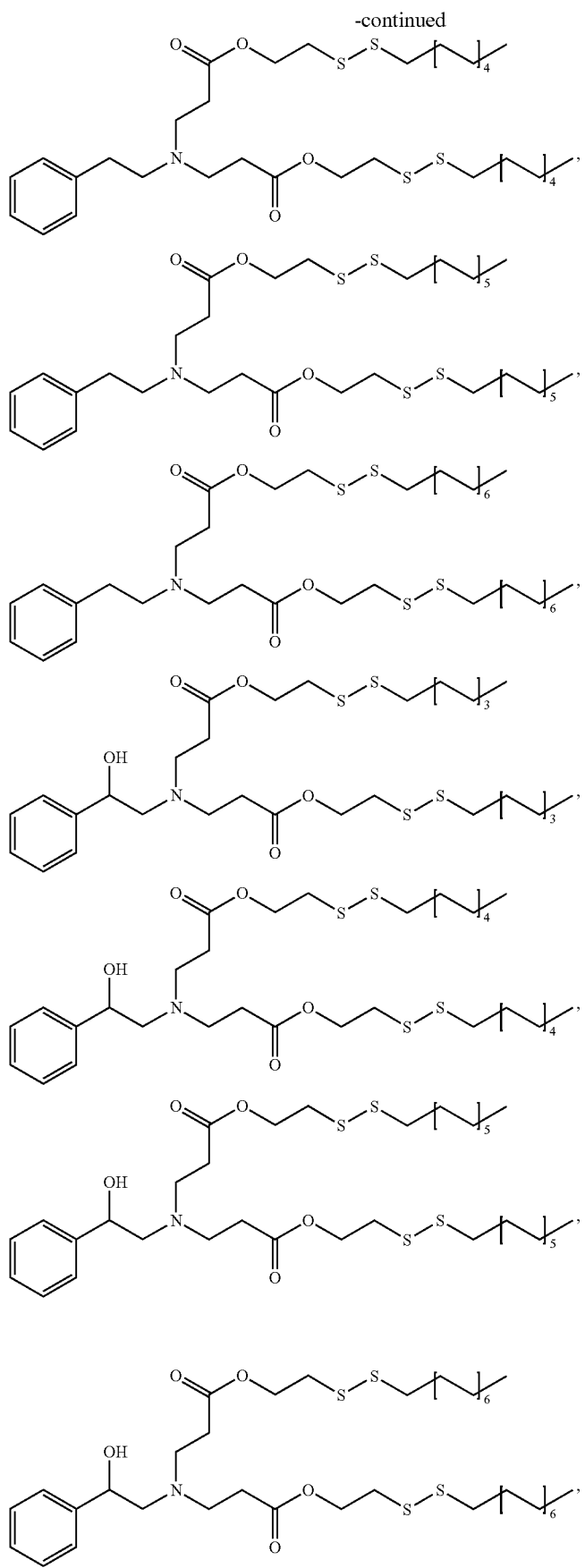

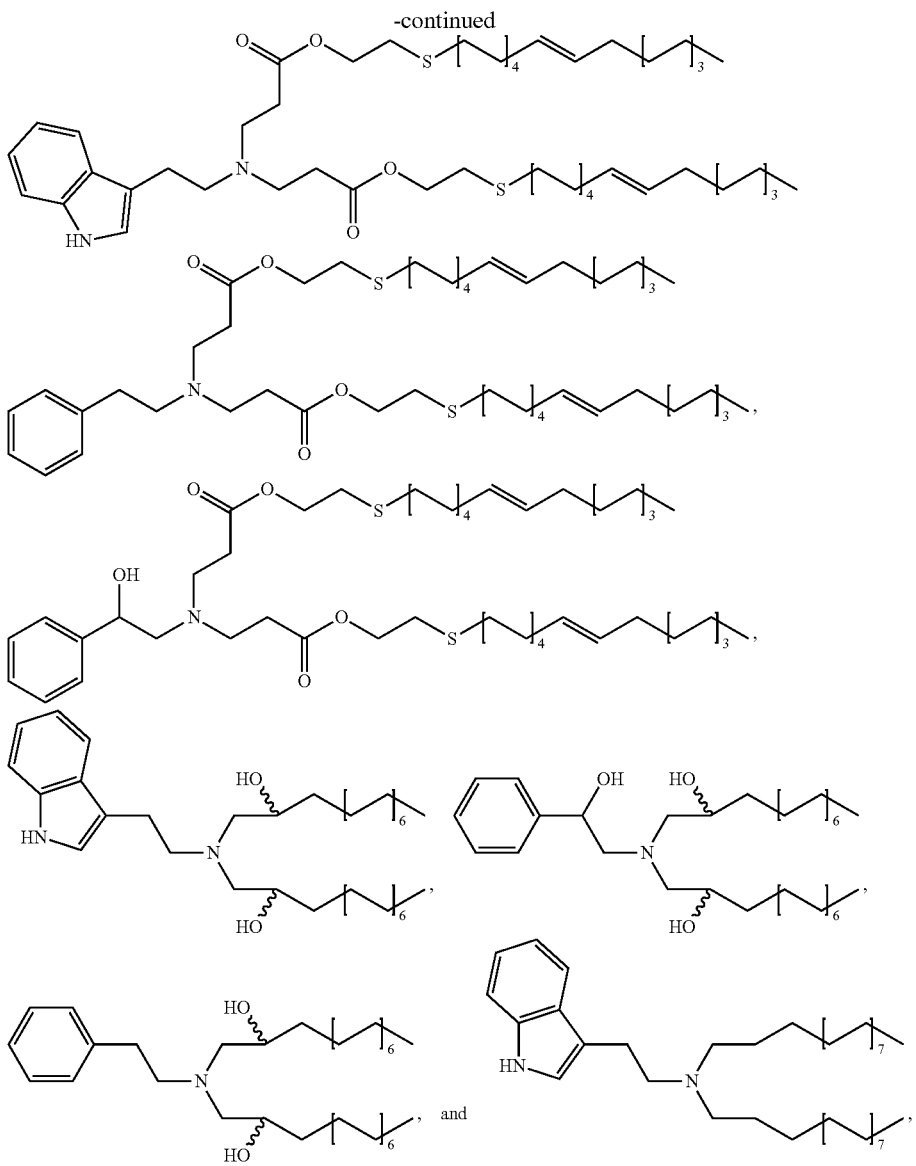

or a pharmaceutically acceptable salt thereof.

In certain aspects, disclosed are lipidoid nanoparticles comprising a compound disclosed herein.

In certain embodiments, the nanoparticle disclosed herein further comprising a protein.

In certain embodiments, the protein is GFP-Cre.

In certain embodiments, the nanoparticle disclosed herein further comprises a nucleic acid.

In certain embodiments, the nucleic acid is Tau-ASOs.

In certain embodiments, the nanoparticle disclosed herein further comprises a small molecule.

In certain embodiments, the small molecule is an antifungal agent or a chemotherapeutic agent.

In certain embodiments, the small molecule is selected from the group consisting of bortezomib, imatinib, gefitinib, erlotinib, afatinib, osimertinib, dacomitinib, daunorubicin hydrochloride, cytarabine, fluorouracil, irinotecan hydrochloride, vincristine sulfate, methotrexate, paclitaxel, vincristine sulfate, epirubicin, docetaxel, cyclophosphamide, carboplatin, lenalidomide, ibrutinib, abiraterone acetate, enzalutamide, pemetrexed, palbociclib, nilotinib, everolimus, ruxolitinib, epirubicin, pirirubicin, idarubicin, valrubicin, amrubicin, bleomycin, phleomycin, dactinomycin, mithramycin, streptozotecin, pentostatin, mitosanes mitomycin C, enediynes calicheamycin, glycosides rebeccamycin, macrolide lactones epotihilones, ixabepilone, pentostatin, salinosporamide A, vinblastine, vincristine, etoposide, teniposide, vinorelbine, docetaxel, camptothecin, hycamtin, pederin, theopederins, annamides, trabectedin, aplidine, and ecteinascidin 743 (ET743).

In certain embodiments, the small molecule is amphotericin B or doxorubicin.

In certain embodiments, the lipidoid nanoparticle has a particle size of about 25 nm to about 1000 nm. In certain embodiments, the lipidoid nanoparticle has a particle size of about 50 nm to about 500 nm.

In certain aspects, disclosed are pharmaceutical compositions comprising a lipidoid nanoparticle disclosed herein; and a pharmaceutically acceptable carrier or excipient.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—CH$_2$—O-alkyl, —OP(O)(O-alkyl)$_2$ or —CH$_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

Articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

As used herein, the term "alkyl" refers to saturated aliphatic groups, including but not limited to C$_1$-C$_{10}$ straight-chain alkyl groups or C$_1$-C$_{10}$ branched-chain alkyl groups. Preferably, the "alkyl" group refers to C$_1$-C$_6$ straight-chain alkyl groups or C$_1$-C$_6$ branched-chain alkyl groups. Most preferably, the "alkyl" group refers to C$_1$-C$_4$ straight-chain alkyl groups or C$_1$-C$_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., C$_{1-30}$ for straight chains, C$_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "C$_{x-y}$" or "C$_x$-C$_y$", when used in conjunction with a chemical moiety, such as, acyl, acyloxy, alkyl, alkenyl, alkynyl, or alkoxy is meant to include groups that contain from x to y carbons in the chain. C$_0$alkyl indicates a hydrogen where the group is in a terminal position, a bond if internal. A C$_{1-6}$ alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS-.

The term "amide", as used herein, refers to a group

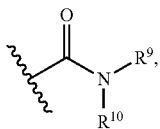

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

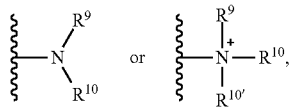

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

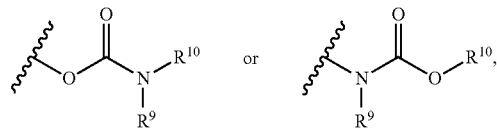

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic.

Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group $-OCO_2-$.

The term "carboxy", as used herein, refers to a group represented by the formula $-CO_2H$.

The term "ester", as used herein, refers to a group $-C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

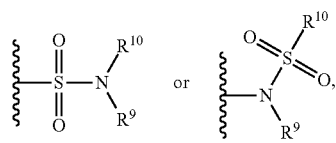

wherein $R^9$ and $R^{10}$ independently represents hydrogen or hydrocarbyl.

The term "sulfoxide" is art-recognized and refers to the group-S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

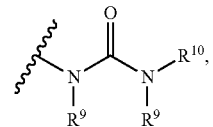

wherein R$^9$ and R$^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Salt" is used herein to refer to an acid addition salt or a basic addition salt.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium potassium, calcium, magnesium, ammonium, tetraalkylammonium, and the like; and when the compound contains a basic functionality, salts of nontoxic organic or inorganic acids, such as hydrochloride, hydrobromide, tartrate, mesylate, acetate, maleate, oxalate and the like.

The term "pharmaceutically acceptable cation" refers to an acceptable cationic counterion of an acidic functional group. Such cations are exemplified by sodium, potassium, calcium, magnesium, ammonium, tetraalkylammonium cations, and the like (see, e. g., Berge, et al., J. Pharm. Sci. 66 (1):1-79 (January 77).

"Pharmaceutically acceptable vehicle" refers to a diluent, adjuvant, excipient or carrier with which a compound of the invention is administered.

"Pharmaceutically acceptable metabolically cleavable group" refers to a group that is cleaved in vivo to yield the parent molecule of the structural formula indicated herein. Examples of metabolically cleavable groups include —COR, —COOR, —CONRR and —CH$_2$OR radicals, where R is selected independently at each occurrence from alkyl, trialkylsilyl, carbocyclic aryl or carbocyclic aryl substituted with one or more of alkyl, halogen, hydroxy or alkoxy. Specific examples of representative metabolically cleavable groups include acetyl, methoxycarbonyl, benzoyl, methoxymethyl and trimethylsilyl groups.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkylesters or (alkoxycarbonyl)oxy)alkylesters. Particularly the $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of the invention.

"Solvate" refers to forms of the compound that are associated with a solvent or water (also referred to as "hydrate"), usually by a solvolysis reaction. This physical association includes hydrogen bonding. Conventional solvents include water, ethanol, acetic acid and the like. The compounds of the invention may be prepared e.g., in crystalline form and may be solvated or hydrated. Suitable solvates include pharmaceutically acceptable solvates, such as hydrates, and further include both stoichiometric solvates and non-stoichiometric solvates. In certain instances, the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

A "subject" to which administration is contemplated includes, but is not limited to, humans (i.e., a male or female of any age group, e.g., a pediatric subject (e.g, infant, child, adolescent) or adult subject (e.g., young adult, middle aged adult or senior adult) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

An "effective amount" means the amount of a compound that, when administered to a subject for treating or preventing a disease, is sufficient to effect such treatment or prevention.

The "effective amount" can vary depending on the compound, the disease and its severity, and the age, weight, etc., of the subject to be treated. A "therapeutically effective amount" refers to the effective amount for therapeutic treatment. A "prophylatically effective amount" refers to the effective amount for prophylactic treatment.

"Preventing" or "prevention" or "prophylactic treatment" refers to a reduction in risk of acquiring or developing a disease or disorder (i.e., causing at least one of the clinical symptoms of the disease not to develop in a subject not yet exposed to a disease-causing agent, or predisposed to the disease in advance of disease onset.

The term "prophylaxis" is related to "prevention," and refers to a measure or procedure the purpose of which is to prevent, rather than to treat or cure a disease. Non limiting examples of prophylactic measures may include the administration of vaccines; the administration of low molecular weight heparin to hospital patients at risk for thrombosis due, for example, to immobilization, and the administration of an anti-malarial agent such as chloroquine, in advance of a visit to a geographical region where malaria is endemic or the risk of contracting malaria is high.

"Treating" or "treatment" or "therapeutic treatment" of any disease or disorder refers, in one embodiment, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^5$N), or the like. It will be understood that, in a compound where such isotopic substitution is made, the following atoms, where present, may vary, so that for example, any hydrogen may be "$^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e., $^3$H, and carbon-14, i.e., $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy. All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of it electrons and an atom (usually H).

For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 95% by weight R-compound and at most about 5% by weight S-compound, at least about 99% by weight R-compound and at most about 1% by weight S-compound, or at least about 99.9% by weight R-compound and at most about 0.1% by weight S-compound. In certain embodiments, the weights are based upon total weight of compound.

As used herein and unless otherwise indicated, the term "enantiomerically pure S-compound" or "S-compound" refers to at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

One having ordinary skill in the art of organic synthesis will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

EXAMPLES

In order that the invention described herein may be more fully understood, the following examples are set forth. The examples described in this application are offered to illustrate the compounds, compositions, materials, device, and methods provided herein and are not to be construed in any way as limiting their scope.

Materials and Methods
General:

All chemicals used for lipid synthesis were purchased from Sigma-Aldrich and directly used as received. All ASOs and DNA fragments were purchased from Integrated DNA Technologies (IDT). The ASOs were used as provided from IDT, and when noted we used the ASO product that is provided by the company to contain chemical modifications to improve stability. HeLa-DsRed and GFP-HEK cells were maintained in Dulbecco's modified eagle's medium (DMEM, Sigma-Aldrich) complemented with 10% fetal bovine serum (FBS, Sigma-Aldrich) and 1% penicillin-streptomycin (Gibco). The fluorescent intensity for GFP-HEK cells was analyzed by flow cytometer (BD FACS Calibur, BD Science, CA). The (−27)GFP-Cre (addgene #89253) protein were expressed and extracted from BL21 *E. coli*, and further purified by Ni-NTA column (Qiagen). Nanoparticle size and ζpotential were recorded on ZetaPALS particle size analyzer. TEM images were captured by a FEI Technai Spirit Transmission Electron Microscope.

Lipid Synthesis

Figure 18A:
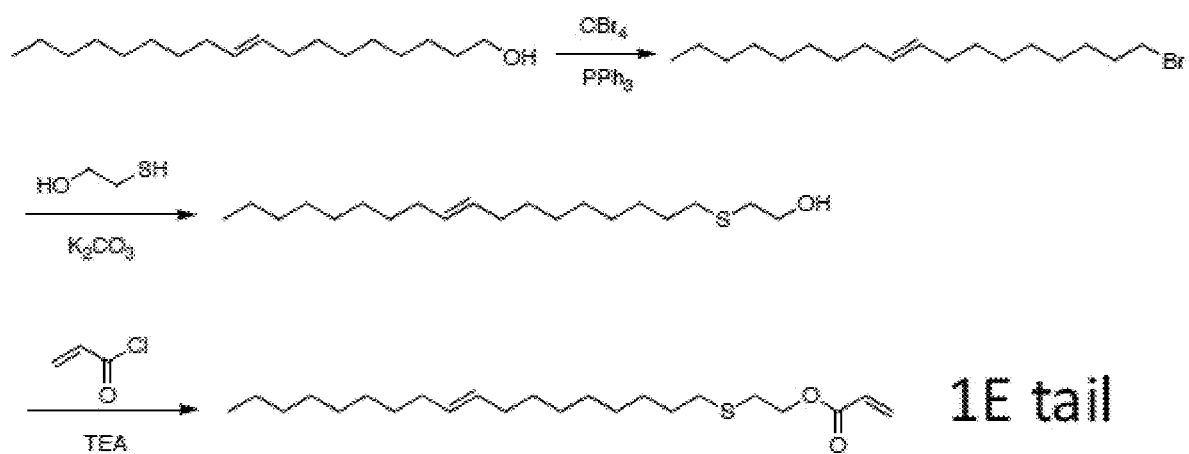
FIG. 18A is a scheme that depicts the synthesis of 1E tail.
Figure 18B:
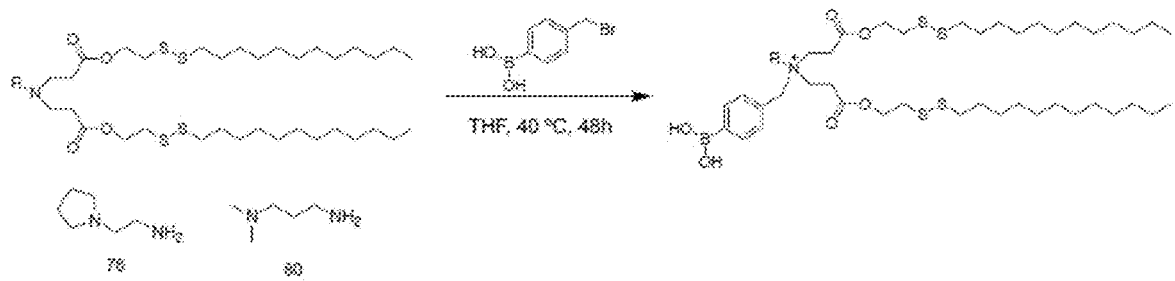
FIG. 18B is a scheme that depicts the synthesis of PBA-Q76016B and PBA-Q80016B.
Figure 18C:
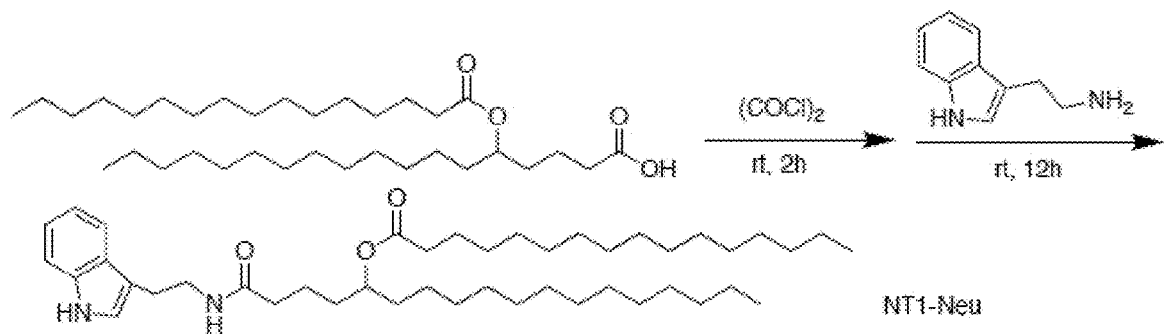
FIG. 18C is a scheme that depicts the synthesis of NT1-Neu.
Figure 19A:
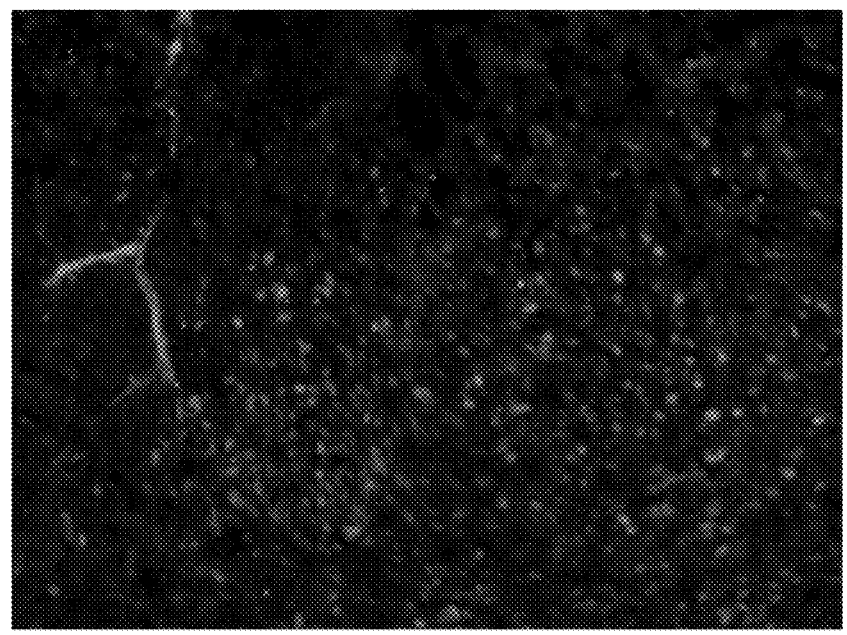
FIGS. 19A-19N are fluorescence images of section of Ail4 mouse brain. The mouse were injected with Cre mRNA complexed with Dlin-MC3/NT1-O14B LNP. The LNP formulation was described in slide 1.
Figure 19B:
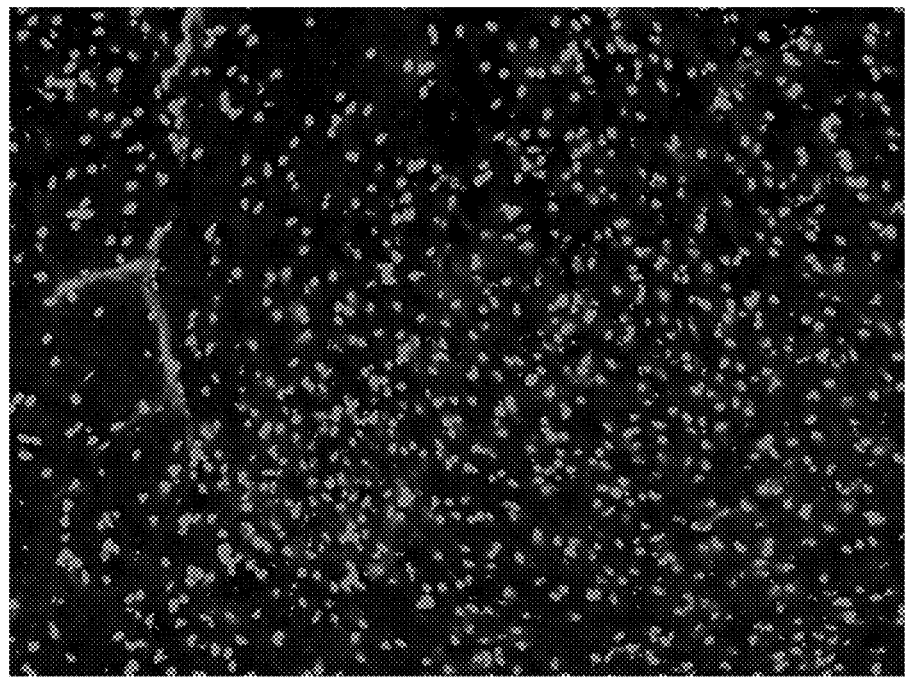
Figure 19C:
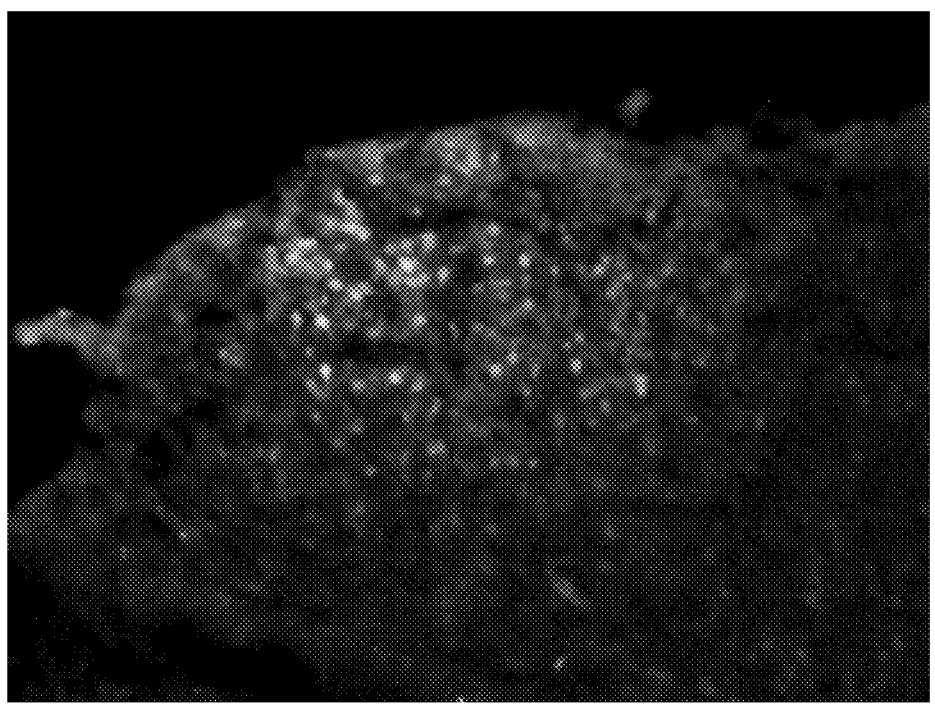
Figure 19D:
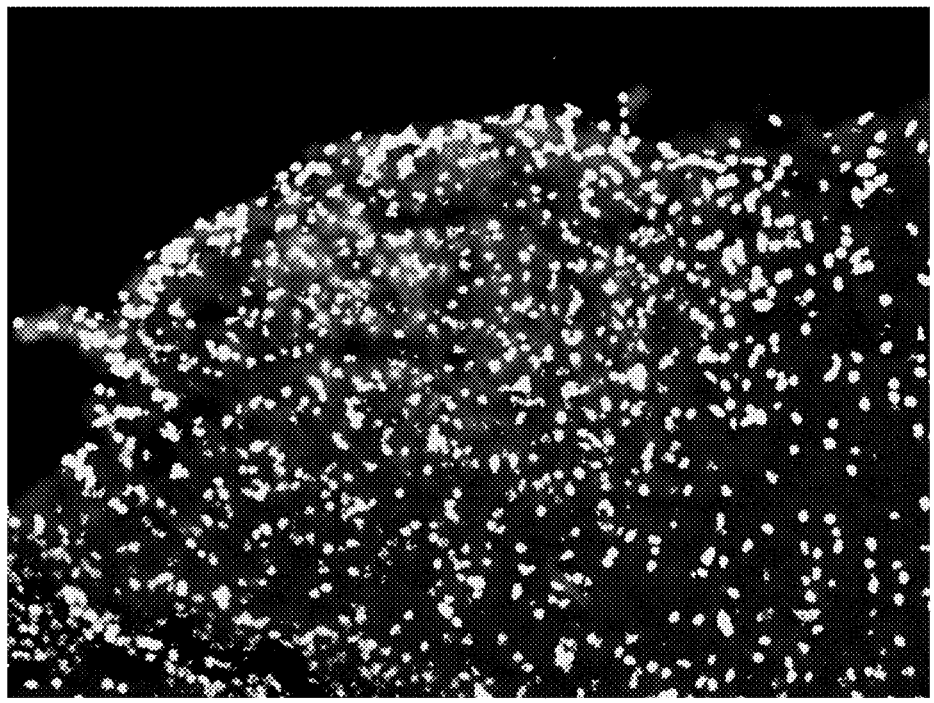
Figure 19E:
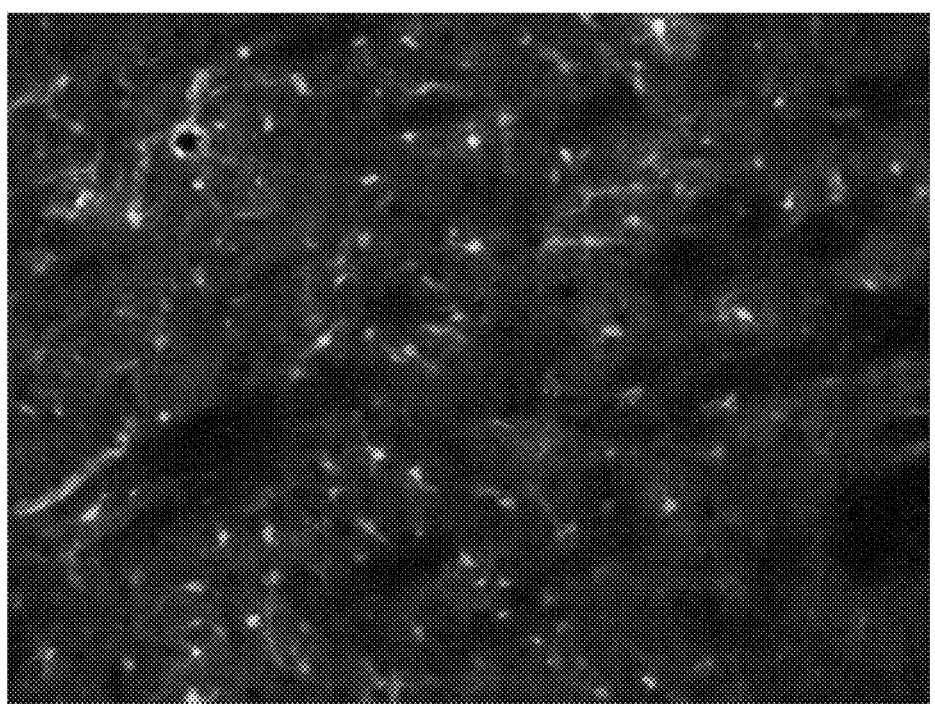
Figure 19F:
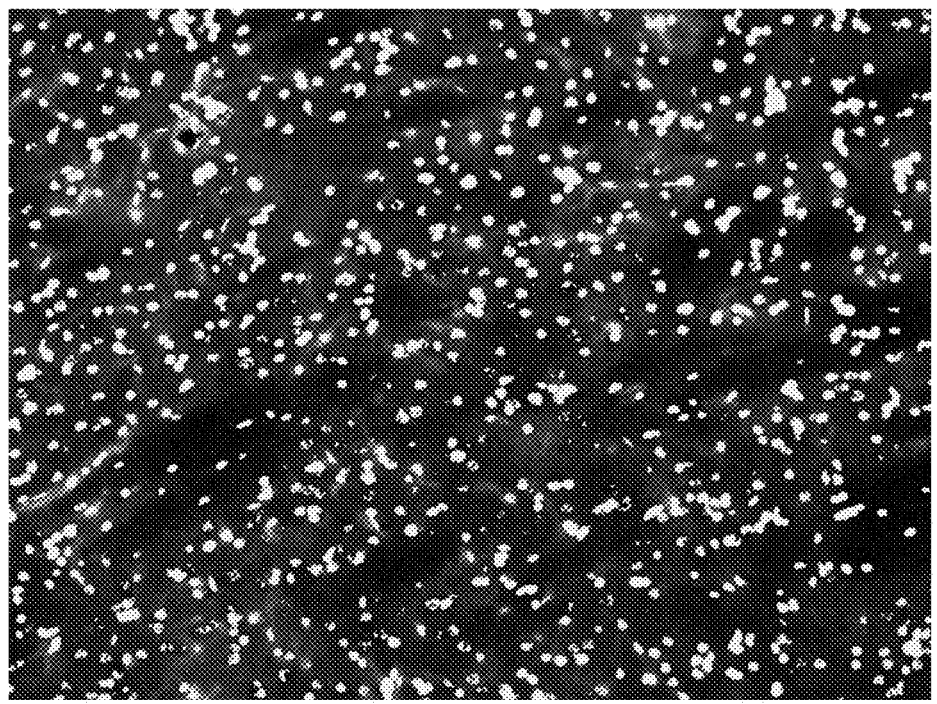
Figure 19G:
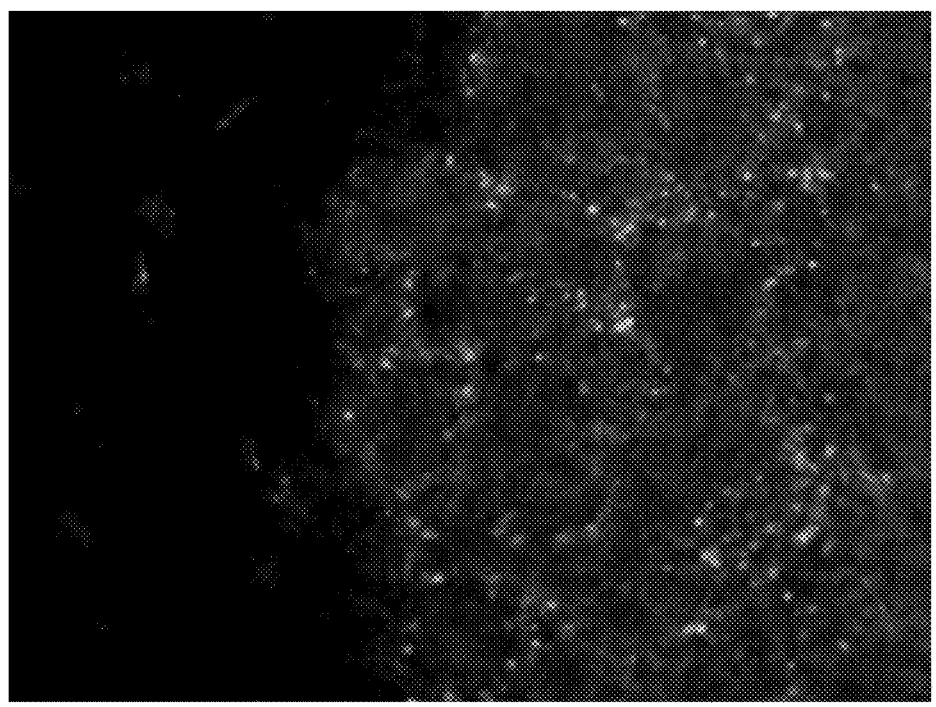
Figure 19H:
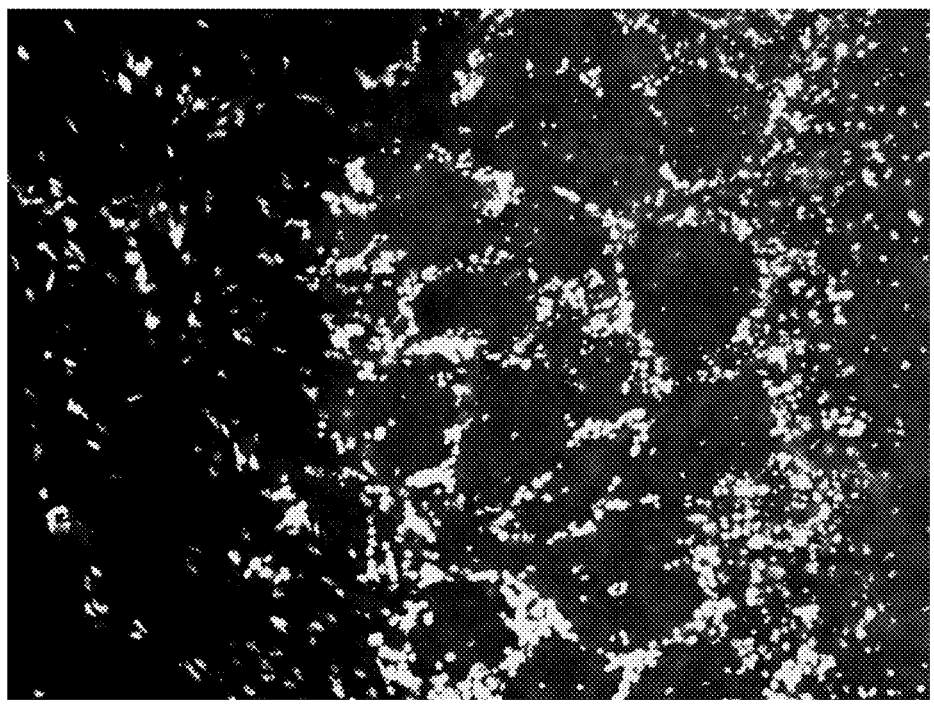
Figure 19I:
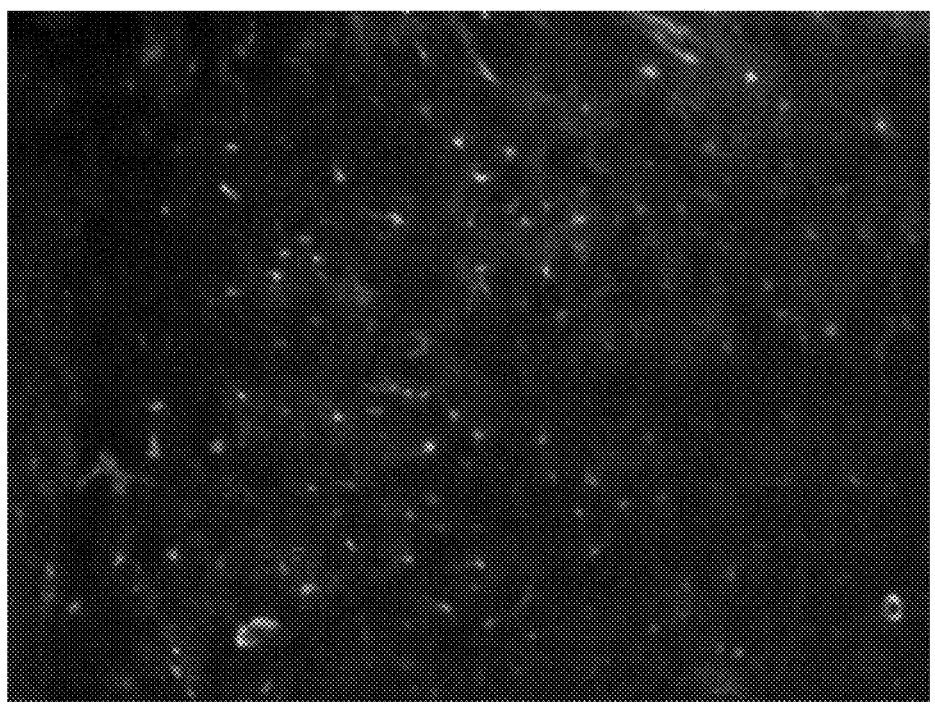
Figure 19J:
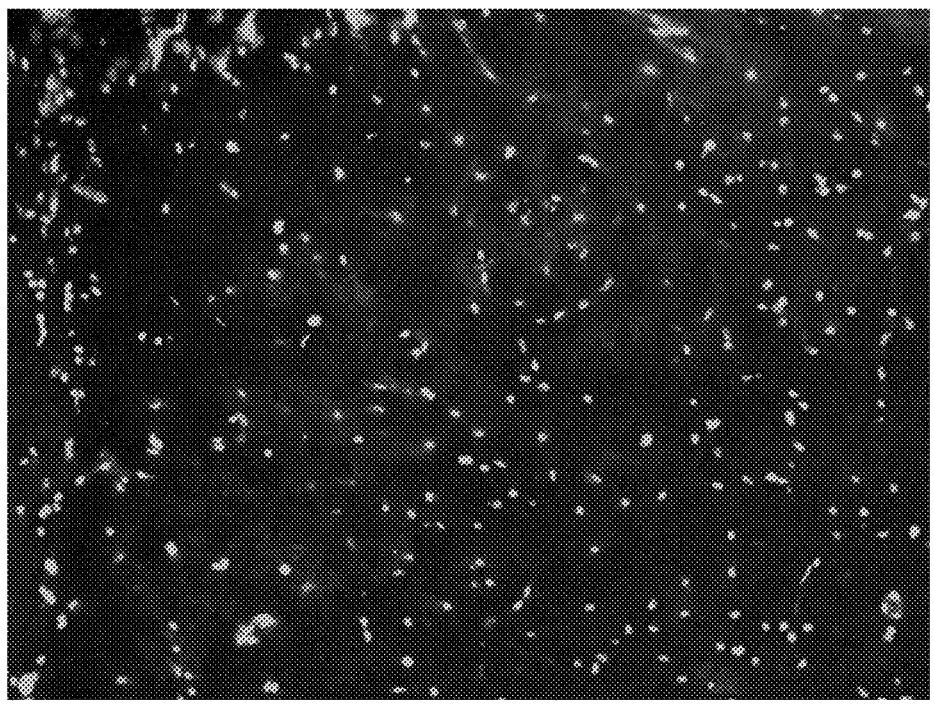
Figure 19K:
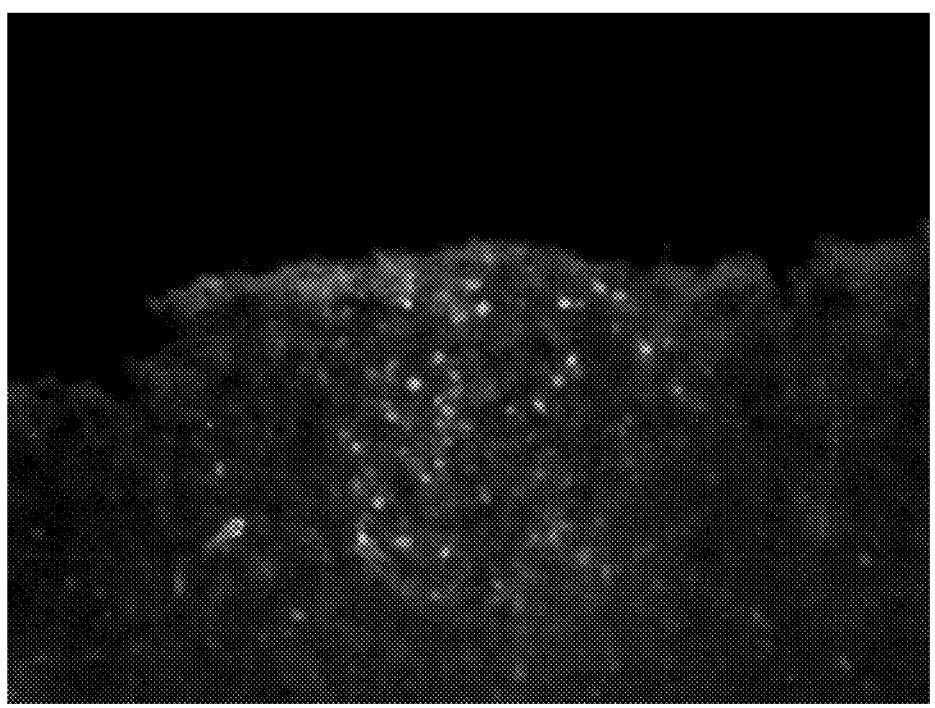
Figure 19L:
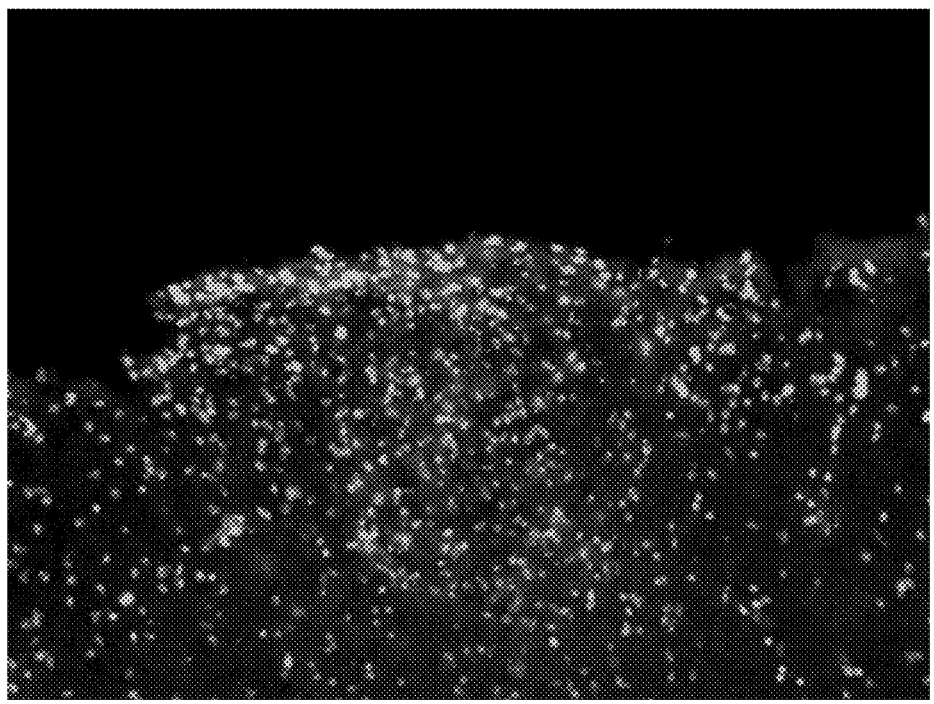
Figure 19M:
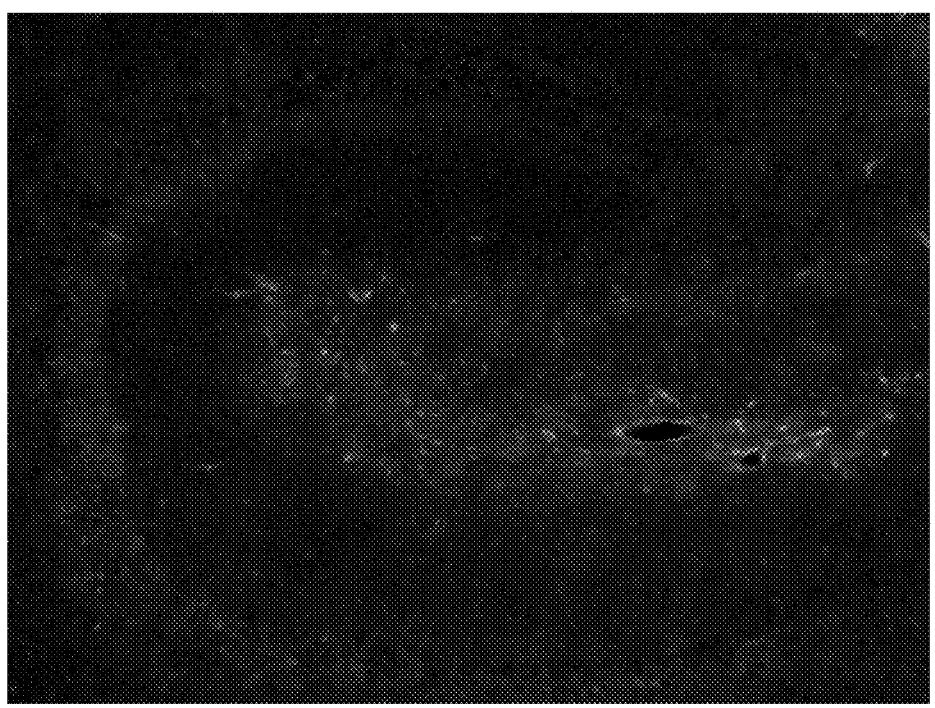
Figure 19N:
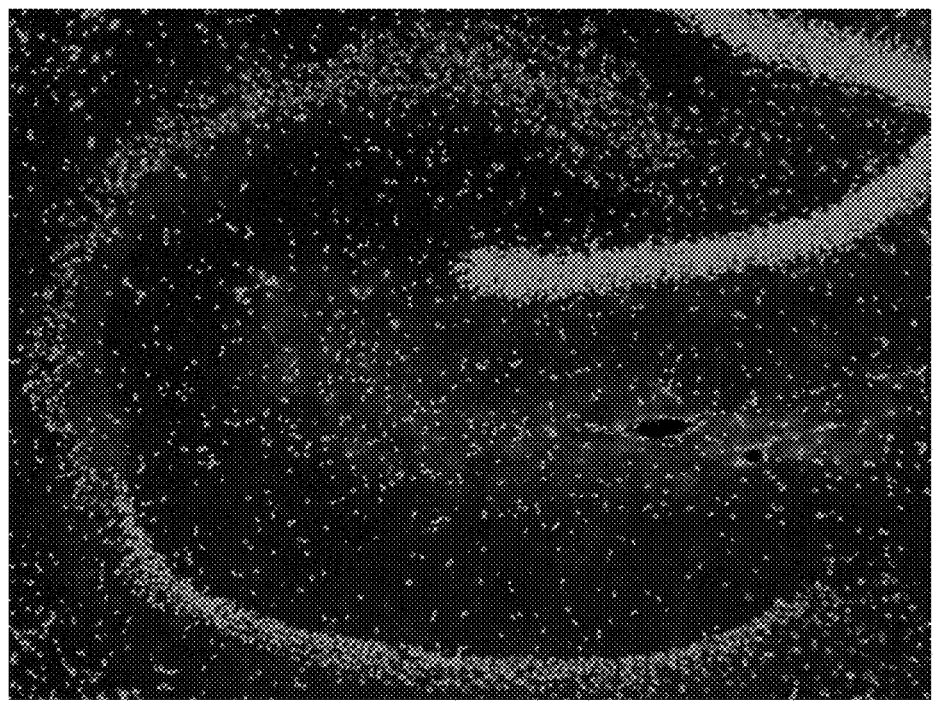
Figure 20A:
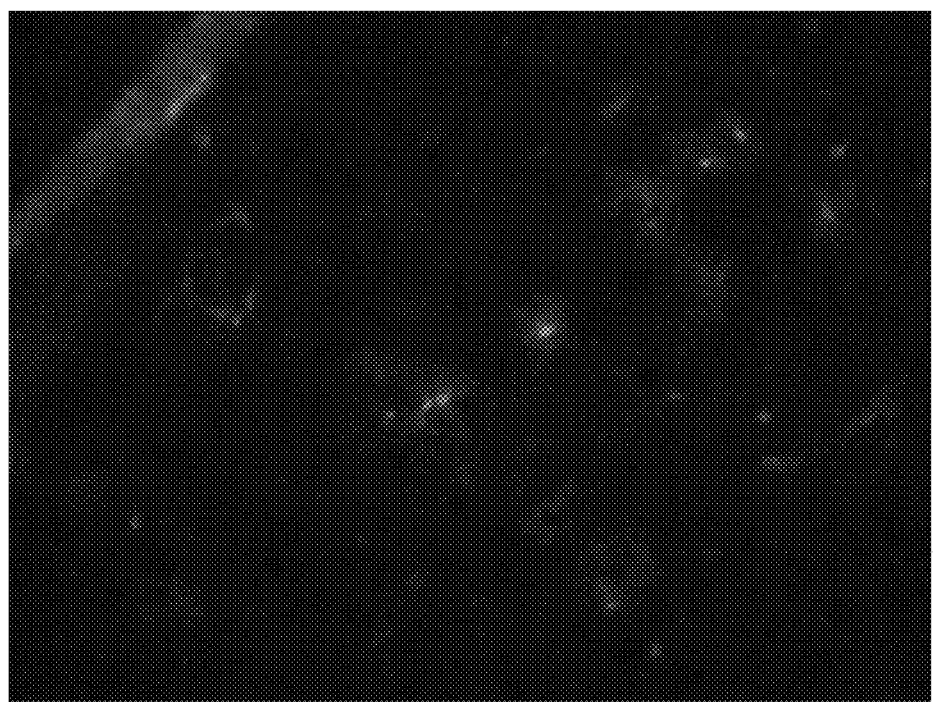
FIGS. 20A-20B are fluorescence images of section of Ail4 mouse brain. The mice were injected with Cre mRNA complexed with PBA-Q76016B/NT1-O14B LNP. The LNP formulation was described in slide 1.
Figure 20B:
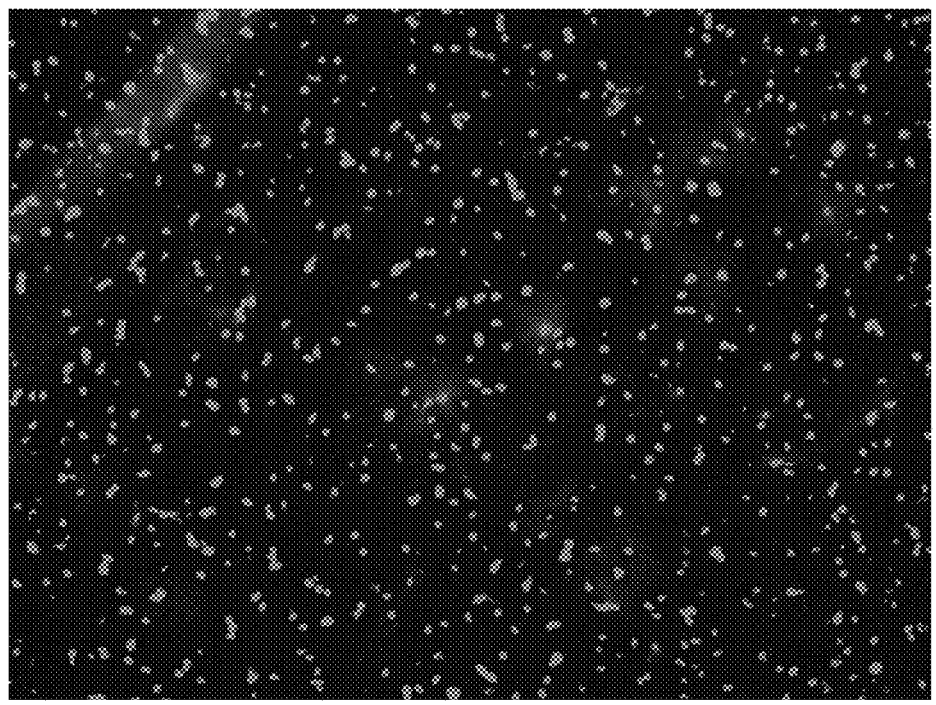
Figure 21A:
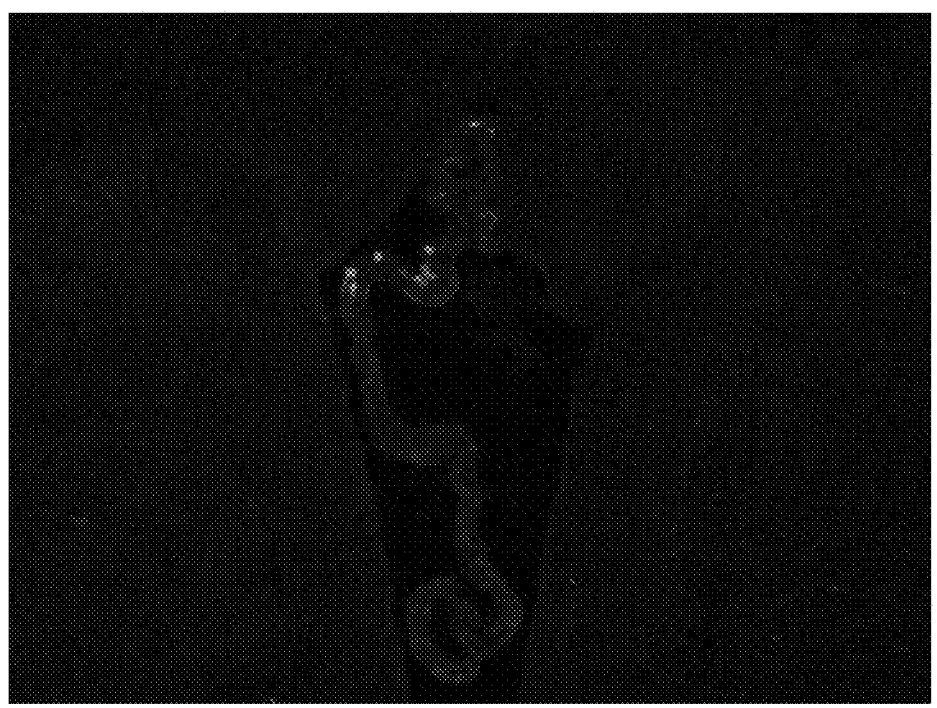
FIGS. 21A-21B are fluorescence images of section of Ail4 mouse brain. The mice were injected with Cre mRNA complexed with Dlin-MC3/NT1-O14B LNP. The LNP formulation was described in slide 1.
Figure 21B:
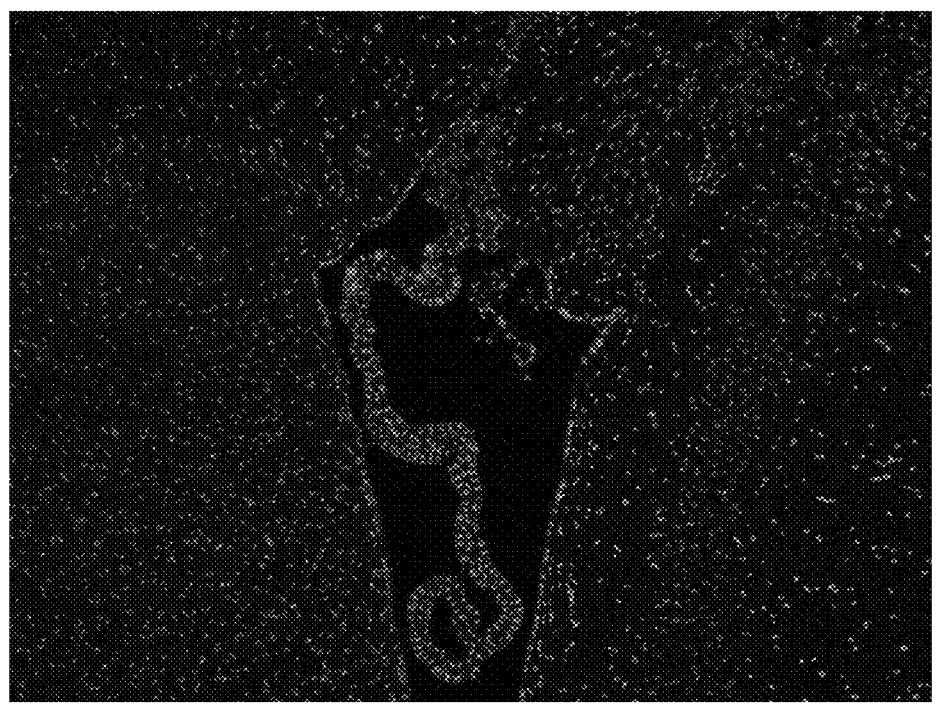

All head amines used for lipid synthesis are commercially available from Sigma-Aldrich. All the cationic lipidoids (NT1-O12B-O18B, NT2-O12B-O18B, NT3-O12B-O18B, NT1-EC16, NT1-$C_{18}$, NT1-1E, NT2-EC16, NT2-1E, NT3-EC16, NT3-1E, 306-O12B-3, 76-O16B) were synthesized according to our previous reports. The crude product was purified using flash chromatography on silica gel. The 1E tail was synthesized as shown in FIG. 18A. The phenylboronic acid quaternized lipidoids were synthesized as shown in FIG. 18B. NT1-Neu was synthesized as shown in FIG. 18C. The lipid structure was confirmed using 1H NMR and electrospray ionization (ESI) MS.

Biodistribution of DiR Labelled NT-LNPs in Mice Brain

The NT-lipidoids and DiR is dissloved at a weight ratio of 10:1, together in 100% ethanol. 100 μL solution was then added dropwise to 300 μL of sodium acetate buffer (25 mM, pH 5.2) and vortexed briefly. Finally, we removed the ethanol in the formulation by dialysis against diH2O (MWCO 35 kDa, ThermoFisher) for 12 h. Then the DiR-labelled LNPs were intravenously injected into BALB/C mice (female, 6 weeks age). After 1 hour, mice were anesthetized and perfused with saline. Afterward, mice brains were collected. The fluorescent signals distribution was visualized using the Spectrum CT Biophotonic Imager (PerkinElmer, Boston, Mass.).

Preparation of AmB/NT-Lipidoid Nanoparticles Formulations

The AmB encapsulates were prepared according to our previous report.3 Briefly, 1 mg each lipidoid (solid) was mixed with 1 mg AmB in 300 μL Dimethyl sulfoxide (DMSO). The mixtures were sonicated for 30 min and then vortexed for 10 min until completely dissolved. The solution was added drop wise to a glass bottle containing 600 μL sodium acetate buffer (pH 5.0) with continuous homogenization at 700 rpm. The solutions were further dialyzed against distilled water to remove DMSO and non-encapsulated AmB using dialysis tubing (MWCO 35 kDa) overnight.

Characterization of AmB/NT-Lipidoid Nanoparticles Formulations

The particle sizes and polydispersity index (PDI) of all encapsulates were measured using dynamic light scattering (DLS). ζpotential were recorded on ZetaPALS particle size analyzer. The DLCs of AmB were calculated according to to our previous report.3 TEM images were captured by a FEI Technai Spirit Transmission Electron Microscope.

Statistical Analysis

Statistical analysis was performed using one-way analysis of variance (ANOVA) followed by the Turkey-Kramer multiple comparison test for more than two groups. Student t-test were used for comparing two groups using Prism (v.8, GraphPad Software, La Jolla, Calif.). Values of p<0.05 were considered as significance.

NT-Lipidoids Synthesis and BBB-Permeability Study of the NT-LNPs

Figure 1B:
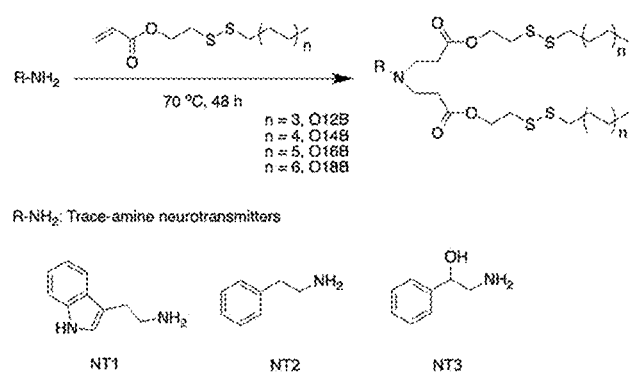
FIG. 1B is a schematic illustration of synthesis route, lipid nomenclature, and chemical structure of neurotransmitters used for lipidoid synthesis.
Figure 5:
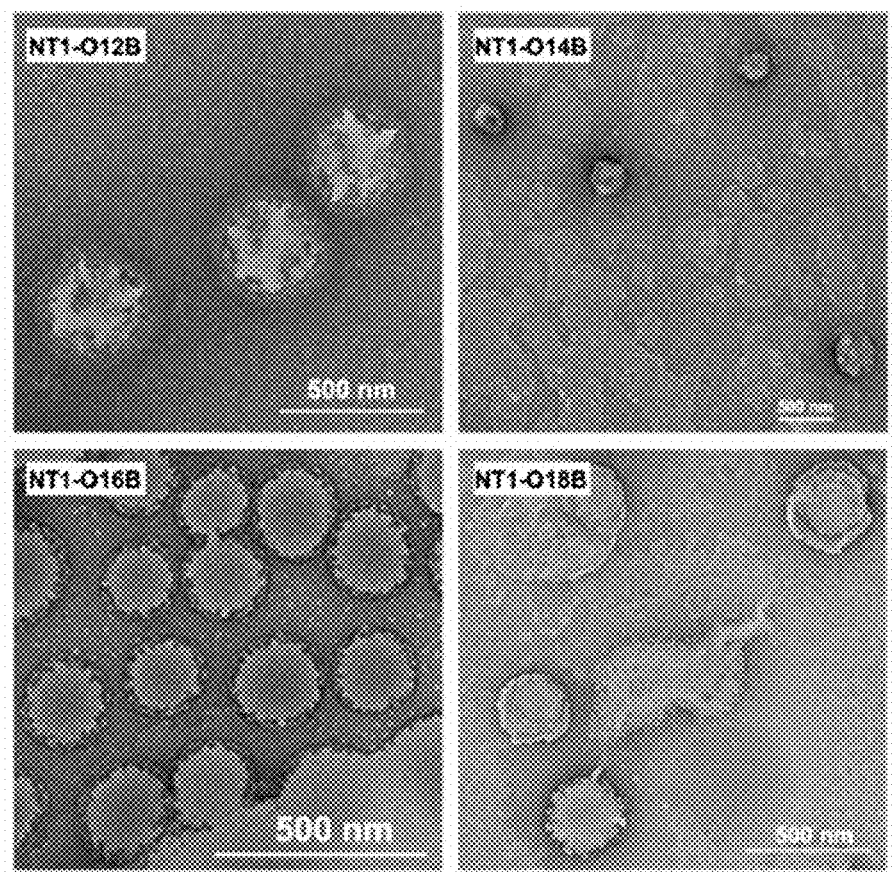
FIG. 5 are TEM images of NT1-LNPs and table of hydrodynamic sizes, polydispersity index, zeta potential.

Neurotransmitters tryptamine, phenethylamine, and phenylethanolamine were selected as the structural basis of the synthetic lipidoids. The NT-lipidoids were synthesized through Michael addition between the primary amine of the neurotransmitters and acrylate-containing hydrophobic tails in glass vials at 70° C. for 48 h (FIG. 1B), using an approach similar to our previously published combinatorial lipid library synthesis strategy. The result is a combinatorial library of NT-lipidoids, each containing one particular neurotransmitter as the head group, and one particular bioreducible hydrophobic structure as the tail group. The NT-lipidoids were named "NTn-O[x]B" (n=1, 2, 3), where NT1 is tryptamine, NT2 is phenethylamine, NT3 is phenylethanolamine, and O[x]B represents the bioreducible hydrophobic tail where [x] indicates the number of carbon atoms in the hydrophobic tail of the acrylate shown in FIG. 1B. For example, NT1-O12B indicates a lipidoid containing a tryptamine head group, and a hydrophobic tail group containing 12 carbon atoms. All the NT-lipidoids were purified using flash chromatography and characterized by ESI-MS (Table 1). The resulting NT-lipidoids are amphiphilic, and thus are capable of self-assembly into either micelles or liposomes when prepared in aqueous solution. Dynamic Light Scattering (DLS) and Transmission Electron Microscopy (TEM) of the NT-lipidoids indicated that these structures indeed self-assembled into spherical liposome-like structures (FIG. 5).

TABLE 1

MS Values of the NT-Derived Lipids Synthesized

| Lipid Structure | Designation | ESI-MS [M + H]+ |
|---|---|---|
| | NT1-O12B | 713.61 |
| | NT1-O14B | 769.61 |
| | NT2-O12B | 674.61 |
| | NT2-O14B | 730.62 |
| | NT1-O16B | 825.70 |
| | NT1-O18B | 881.75 |

TABLE 1-continued

MS Values of the NT-Derived Lipids Synthesized

| Lipid Structure | Designation | ESI-MS [M + H]+ |
|---|---|---|
| | NT2-O16B | 786.64 |
| | NT2-O18B | 842.72 |
| | NT3-O12B | 690.55 |
| | NT3-O14B | 746.65 |
| | NT1-Neu | 681.52 |
| | NT1-1E | 925.82 |

TABLE 1-continued
MS Values of the NT-Derived Lipids Synthesized
| Lipid Structure | Designation | ESI-MS [M + H]+ |
|---|---|---|
| 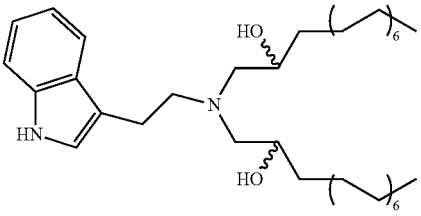 | NT1-EC16 | 641.82 |
| 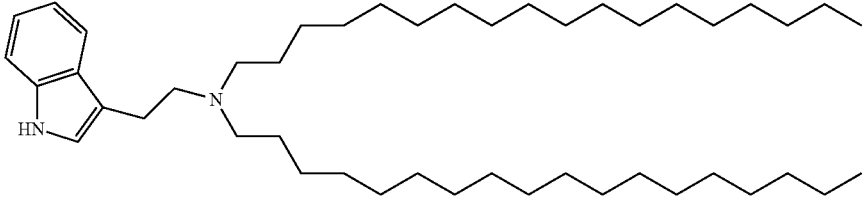 [SMILES: CCCCCCCCCCCCCCCCCCN(CCCCCCCCCCCCCCCCCC)CCc1c[nH]c2ccccc12] | NT1-C18 | 665.91 |
| 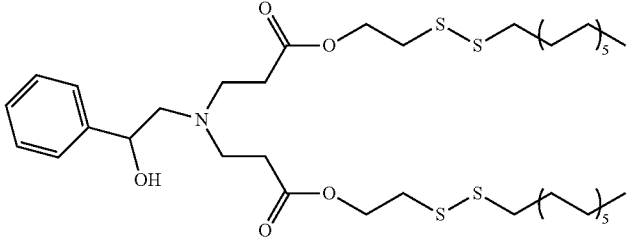 | NT3-O16B | 802.73 |
| 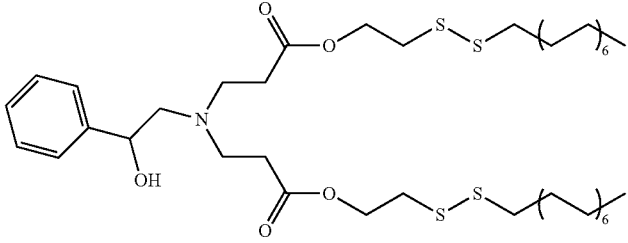 | NT3-O18B | 858.73 |
| 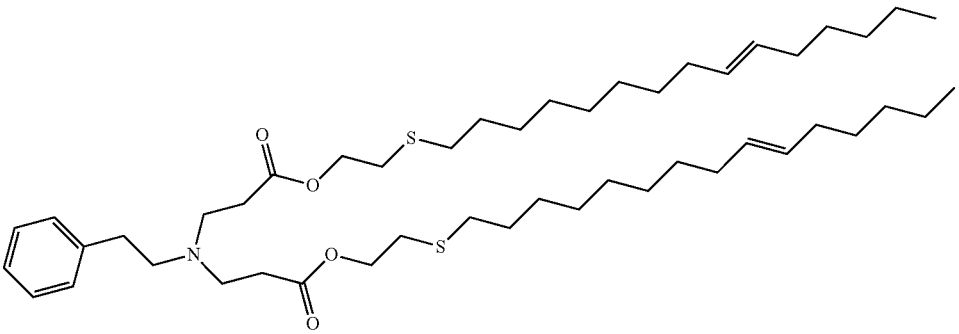 [SMILES: CCCCC/C=C/CCCCCCCCSCCOC(=O)CCN(CCC(=O)OCCSCCCCCCCC/C=C/CCCCC)CCc1ccccc1] | NT2-1E | 886.82 |

TABLE 1-continued
MS Values of the NT-Derived Lipids Synthesized
| Lipid Structure | Designation | ESI-MS [M + H]+ |
|---|---|---|
| 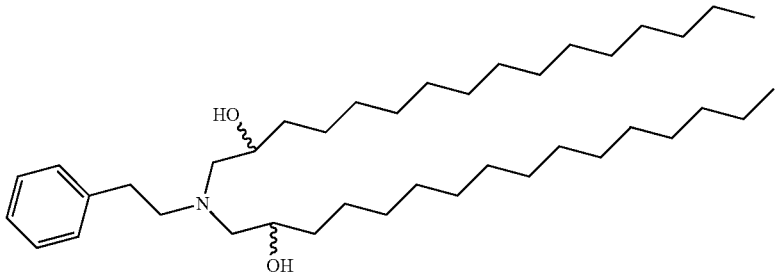 [SMILES: CCCCCCCCCCCCCCC(O)CN(CCc1ccccc1)CC(O)CCCCCCCCCCCCCC] | NT2-EC16 | 602.82 |
| 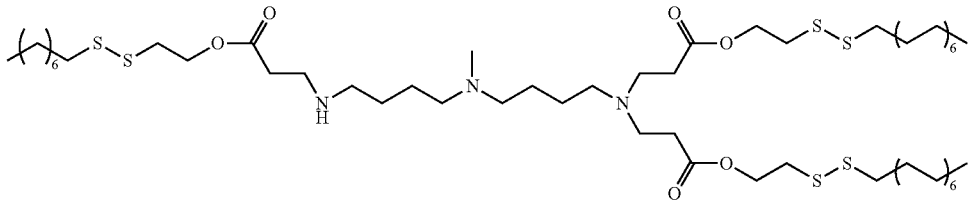 | 306-O12B3 | 974.73 |
| 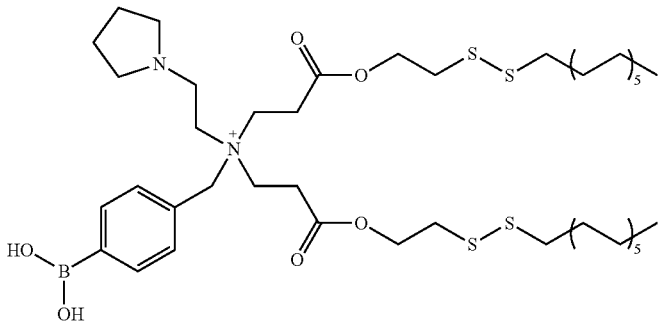 | PBA-Q76-O16B | 913.73 |
| 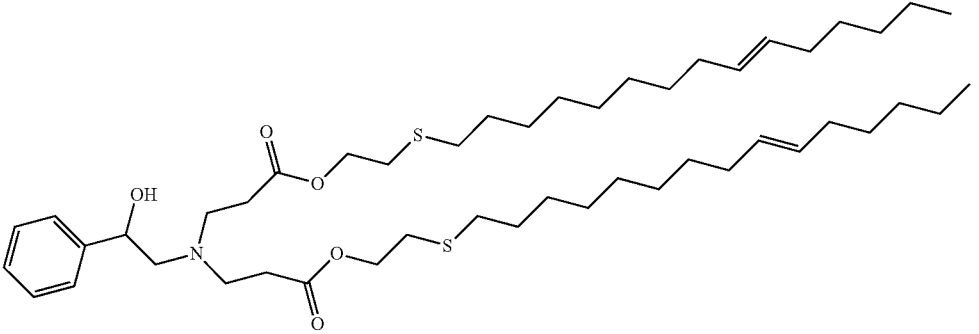 [SMILES: CCCCC/C=C/CCCCCCCCSCCOC(=O)CCN(CCC(=O)OCCSCCCCCCCC/C=C/CCCCC)CC(O)c1ccccc1] | NT3-1E | 902.91 |
| 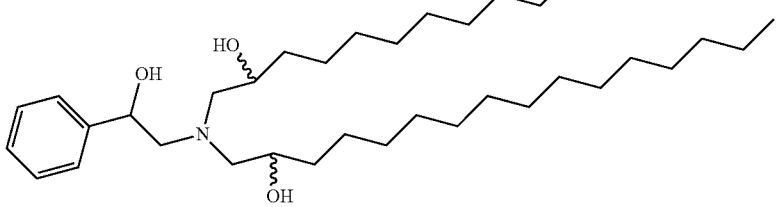 | NT3-EC16 | 618.82 |

Whether these NT-lipidoids can cross the BBB upon systemic intravenous delivery, using a fluorescent dye (DiR) as a model cargo was further studied. Hydrophobic small molecules such as DiR can partition into the hydrophobic region of micelles and liposomes and have often been used to track the biodistribution of these structures. To formulate the DiR-loaded NT-lipidoids, the NT-lipidoid and DiR were mixed in ethanol in a 10/1 (w/w) ratio, added the mixture dropwise to sodium acetate buffer (25 mM, pH 5.2), and then removed the ethanol through dialysis. The DiR-loaded NT-lipidoid nanoparticle solution was injected into mouse via tail vein injection. After 1 h, the animals were sacrificed and perfused with saline. The skull was removed, and the brain was imaged using an IVIS imaging device (PerkinElmer) at the excitation wavelength of 750 nm.

Figure 1C:
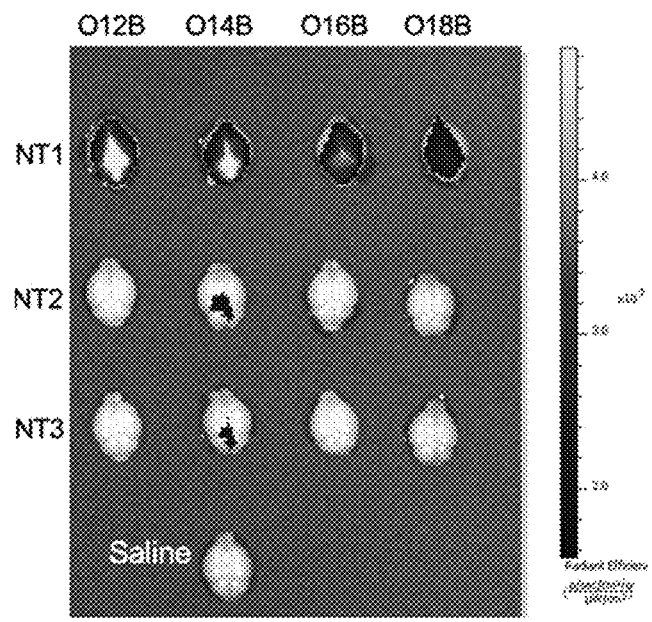
FIG. 1C is a representative ex vivo fluorescence images of the dissected brain 1 h after one-time intravenous injection of 1 mg kg$^{-1}$ DiR-labeled NT-LNPs. DiR was doped into the NT-LNPs with a 10% weight ratio. The mice were perfused with saline before dissection.
Figure 6:
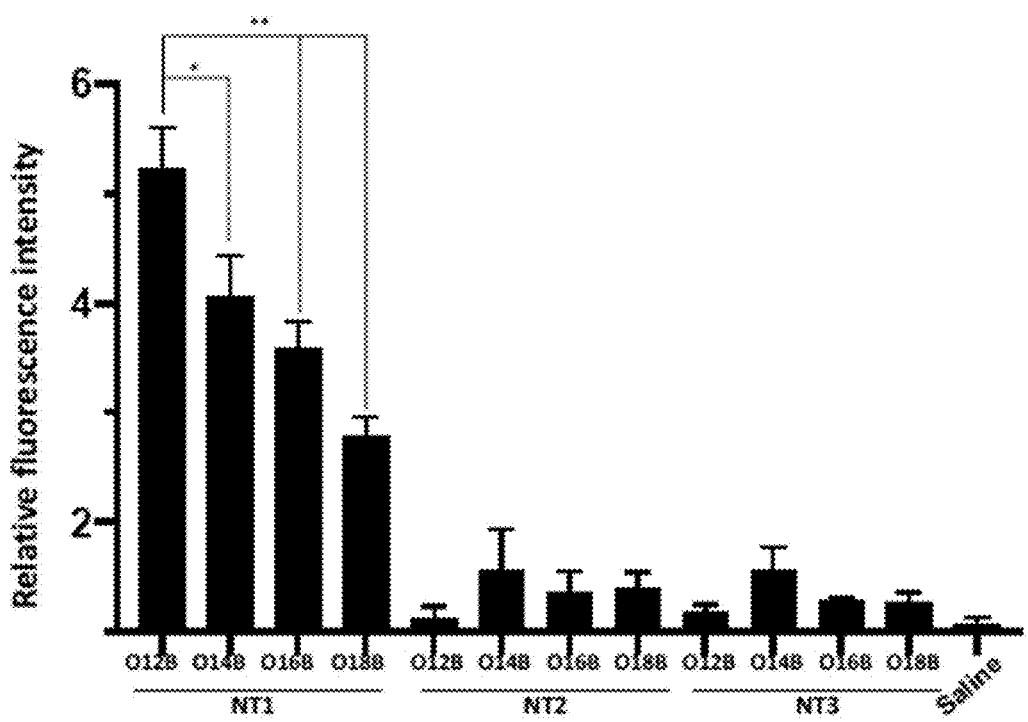
FIG. 6 is graph summarizing relative fluorescence intensity of the dissected brain tissue 1 h after one-time intravenous injection of 1 mg kg-1 DiR-labeled NT-LNPs. DiR was doped into the NT-LNPs with a 10% weight ratio. The mice were perfused with saline before dissection. One-way ANOVA, Sidak post hoc analysis, *p<0.05 or **p<0.01.

As shown in FIG. 1C, strong DiR fluorescence signal is observed in the mouse brain treated with DiR/NT1-lipidoid nanoparticles, compared to the mouse brain treated with DiR/NT2-lipidoids and DiR/NT3-lipidoids where the fluorescent signal was very weak. It is also observed that length of the aliphatic tail chain significantly influenced the observed fluorescent intensity, with NT1-lipidoids containing a shorter aliphatic chain length resulting in a greater fluorescence intensity (FIG. 6). There is no significant difference of the physical properties, such as hydrodynamic sizes, polydispersity index, zeta potential, and morphologies between these NT1 derived lipidoids (FIG. 5).

Figure 7:
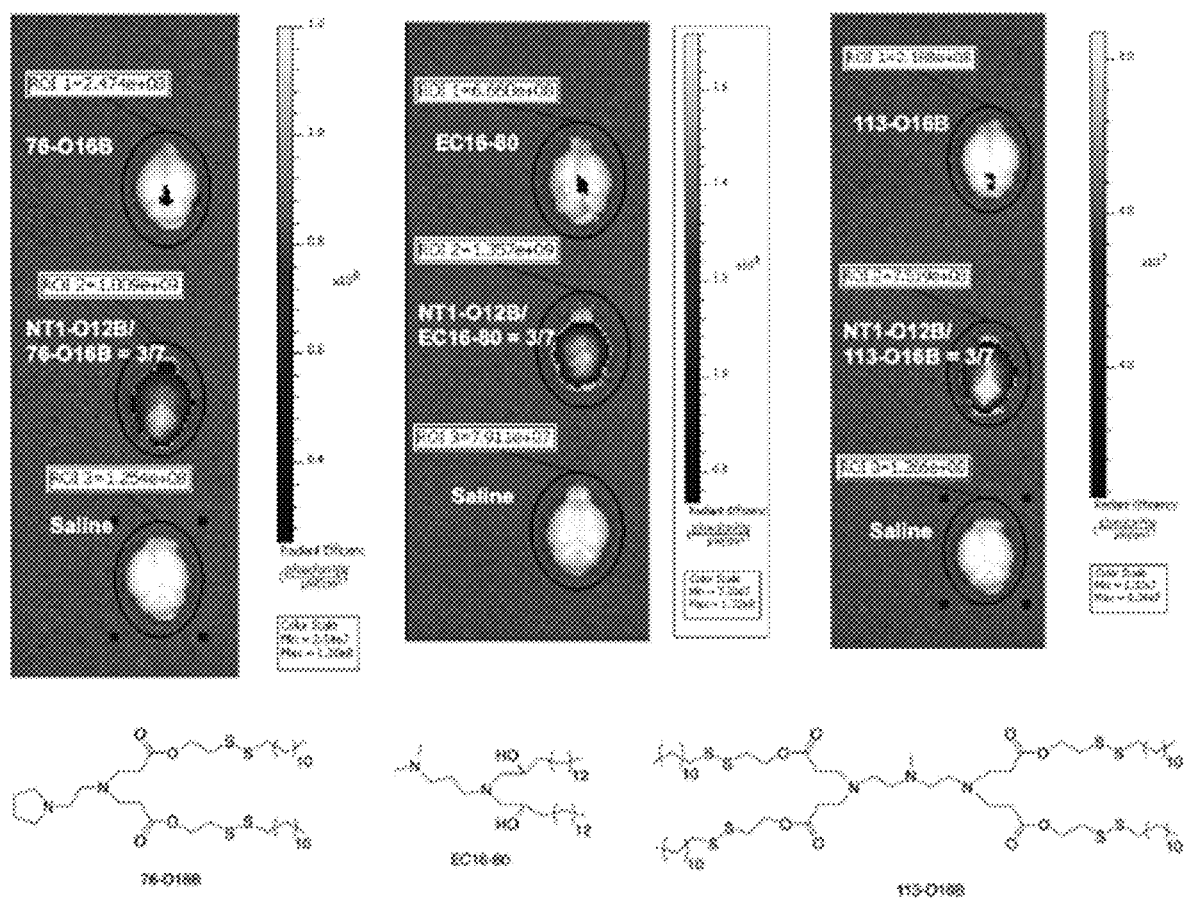
FIG. 7 are representative ex vivo fluorescence images of the dissected brain 1 h after one-time intravenous injection of 1 mg kg-1 DiR-labeled LNPs or NT1-O12B doped NTLNPs (ratio 3:7, w/w), and the chemical structure of 76-O16B, EC16-80, and 113-O16B. DiR was doped into the NT-LNPs with a 10% weight ratio. The mice were perfused with saline before dissection.

It is hypothesized that doping NT1-lipidoids such as NT1-O12B into other BBB-impermeable lipid formulations led to the resulting lipid formulation crossing the BBB. The previously published synthetic lipids, 76-O16B, EC16-80, and 113-O16B, were used to test this ability to deliver DiR to the brain. It is found that none of these lipids were effective in delivering the DiR into the mouse brain by themselves, however, after doping these lipids with the NT1-O12B, strong DiR signals could be observed in the mouse brain (FIG. 7).

Figure 8:
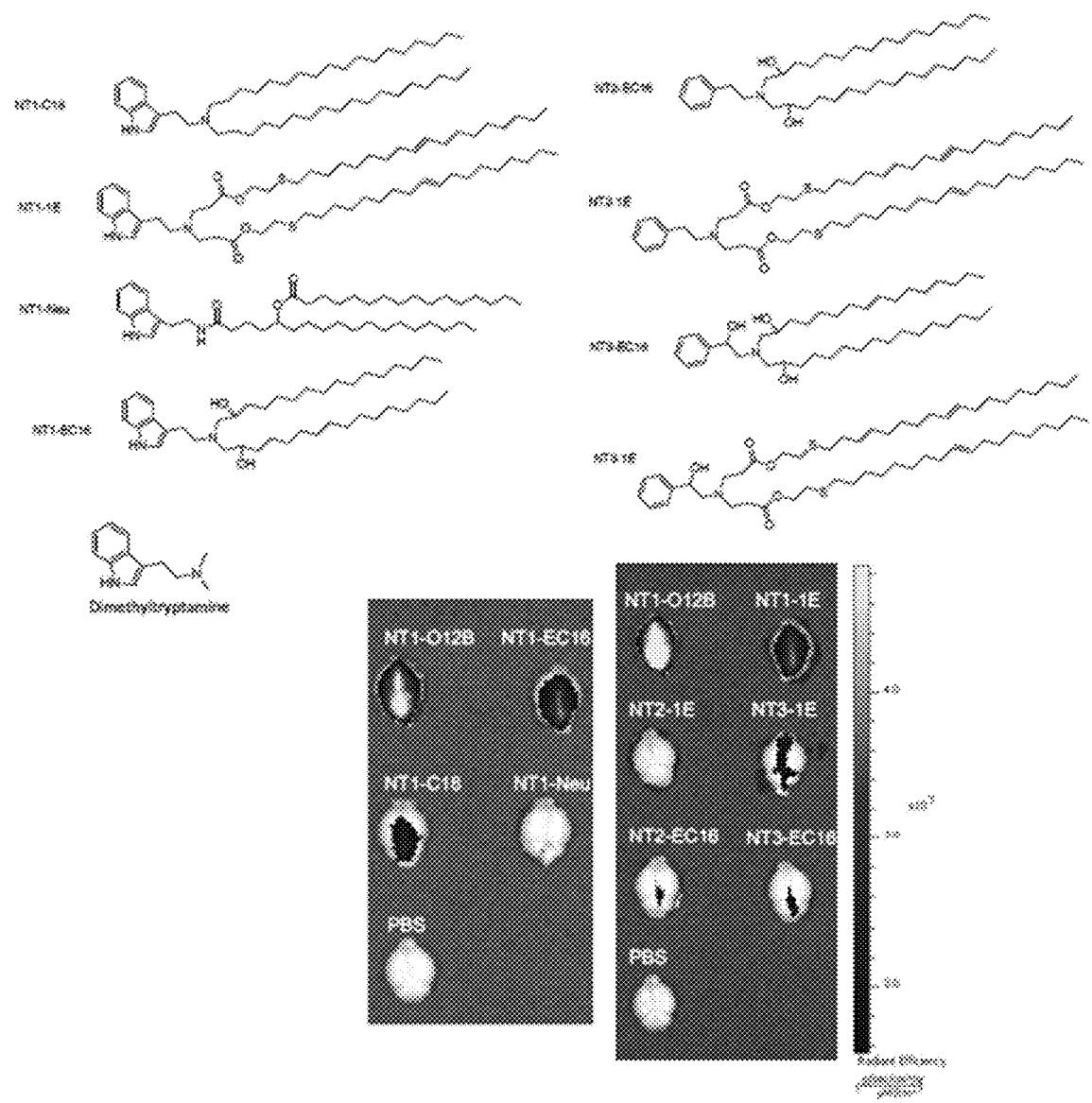
FIG. 8 depicts the chemical structures of NT-lipidoids and dimethyltryptamine, and the representative ex vivo fluorescence images of the dissected brain 1 h after one-time intravenous injection of 1 mg kg-1 DiR-labeled NT-LNPs. DiR was doped into the NTLNPs with a 10% weight ratio. The mice were perfused with saline before dissection.

The chemical structure of NT1 is based on the neurotransmitter dimethyltryptamine which has been reported to cross the BBB by active transport across the endothelial plasma membrane.[21] It is hypothesized that our results are also driven by active transport, and that changes in the chemical structure of the NT1-lipid would modulate its ability to cross the BBB. We hypothesized specifically that the ionizability of the α-amine in the tryptamine (NT1) after the lipidization is an important factor for the derivatives to cross BBB. To verify this hypothesis, a series of NT1 derivatives with different linkers were synthesized, as shown in FIG. 8. The DiR signals were observed from the mouse brain treated with all NT1 derivatives except NT1-neu. In NT1-neu, the α-amine in the tryptamine is connected through an amide bond, not ionizable, while the α-amine in other NT1 derivatives are all ionizable. Further, no strong DiR signals were observed from the mouse brain treated with NT2 and NT3 derived lipidoids with any linkers.

Delivery of Small Molecule AmB into the Mouse Brain

As shown above, NT1 derived lipidoids are identified to be able to deliver a hydrophobic dye (DiR) into brain, either when used alone or when doped into other LNPs. Delivering therapeutically relevant hydrophobic drug molecules into brain was examined using these NT1-derived lipidoids. Amphotericin B (AmB) was chosen as a model drug. AmB is a classic polyene antifungal drug and is the gold standard for the treatment of severe systemic fungal infections. However, it cannot be used clinically for the treatment of brain fungal infections due to its BBB-impermeability. Recently, AmB was formulated in synthetic lipidoid nanoparticles and conducted a thorough PK and biodistribution study of the AmB formulations using traditional synthetic lipid nanoparticles, but in that study none of our lipid nanoparticles were capable of permeating the BBB to deliver AmB into the mouse brain.[27]

Figure 9:
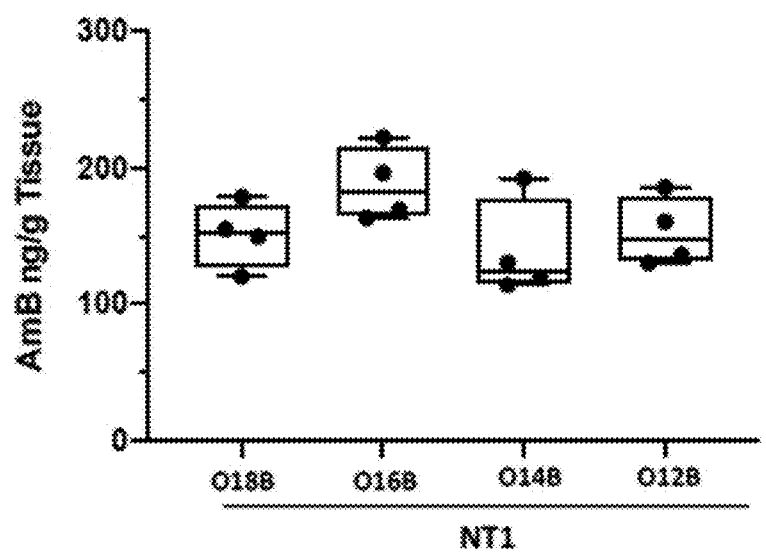
FIG. 9 is a graph depicting AmB concentration in brain tissues 24 h after intravenous injection of 5 mg/kg AmB in various NT1 derivatives measured using HPLC. The mice were perfused with saline before dissection.

AmB was encapsulated in pure NT1-lipidoids (namely NT1-O12B, NT1-O14B, NT1-O16B, and NT1-O18B) using a procedure similar to the DiR encapsulation. The AmB loaded NT1-lipidoid nanoparticles were injected into mice via tail vein at a dose of 5 mg/kg AmB per mouse. After 24 hr, animals were sacrificed, and the brains were harvested, perfused with saline, and homogenized. The AmB concentration in brain tissue was quantified using HPLC. As shown in FIG. 9, the AmB concentration in the brain tissue of all the four groups was around 150 ng/g tissue. Notably, in our previous report, AmB was undetectable in the brain after systemic delivery with traditional synthetic lipidoids, indicating the NT1-lipidoid formulations enhanced the AmB delivery to the mouse brain.

Figure 10A:
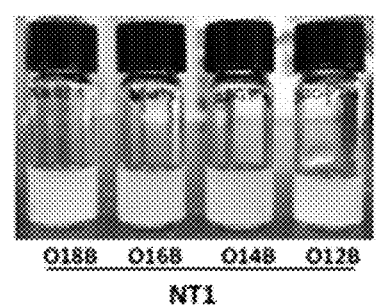
FIG. 10A is a photograph of AmB formulations in NT1-lipidoids with different tail lengths (O18B, O16B, O14B, O12B). All four NT1/AmB encapsulates showed opaque suspension.
Figure 10B:
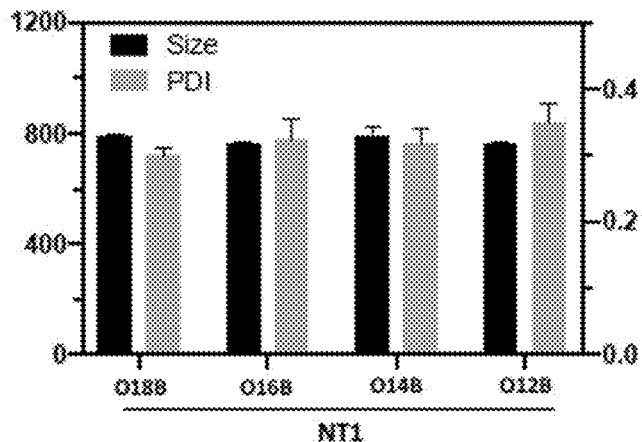
FIG. 10B is a graph depicting hydrodynamic diameters and polydispersity indexes of NT-LNPs determined by DLS measurements.

However, the AmB formulated in NT-lipidoid formulation showed opaque solution (FIG. 10A), indicating the large size of the particles in the solution. DLS results (FIG. 10B, FIG. 11) showed that the nanoparticles are in range of 750-800 nm in diameter. It is hypothesized that making NT1-lipidoid nanoparticle smaller may help improve the brain delivery efficiency. In the previous report, it is found that the quaternized lipidoids provided stable AmB formulation with smaller particle size, comparing with the non-quaternized lipids.[27] Thus, it is hypothesized that doping a quaternized lipidoid with NT1-lipidoid may result in a smaller nanoparticle size while maintaining or improving the ability to penetrate the BBB.

Figure 2A:
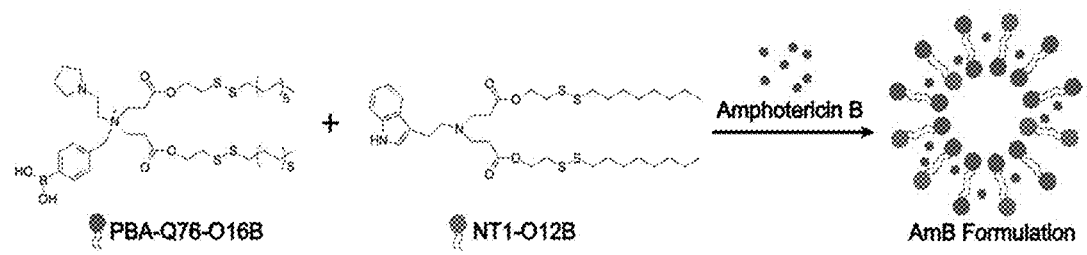
FIG. 2A is chemical structure of PBA-Q76-O16B, NT1-O12B, and schematic illustration of the doped NT1-lipidoid AmB formulation.
Figure 2B:
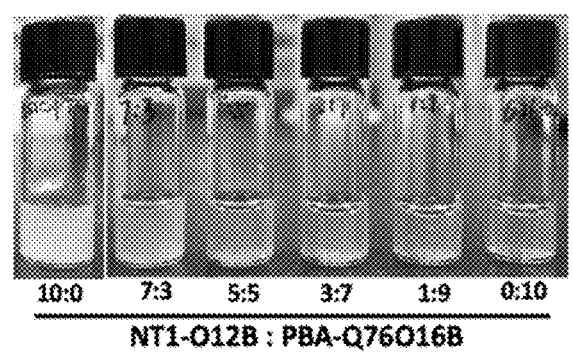
FIG. 2B are photographs of AmB formulations in NT1-O12B doped with different amounts of PBA-Q76O16B (weight ratio is used). The pure NT1-O12B/AmB encapsulates appeared as an opaque suspension, while the appearance of the encapsulates changed from translucent solutions to homogenous transparent yellow solutions as the doping ratio of PBA-Q76-O16B lipidoid increased.
Figure 2C:
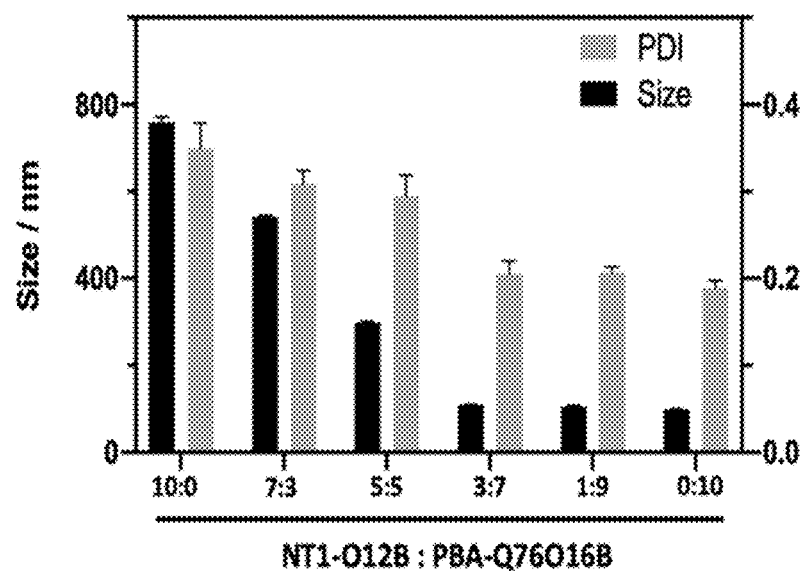
FIG. 2C is graph depicting hydrodynamic diameters and polydispersity indexes of different NT-LNP/AmB formulations determined by DLS measurements.
Figure 2D:
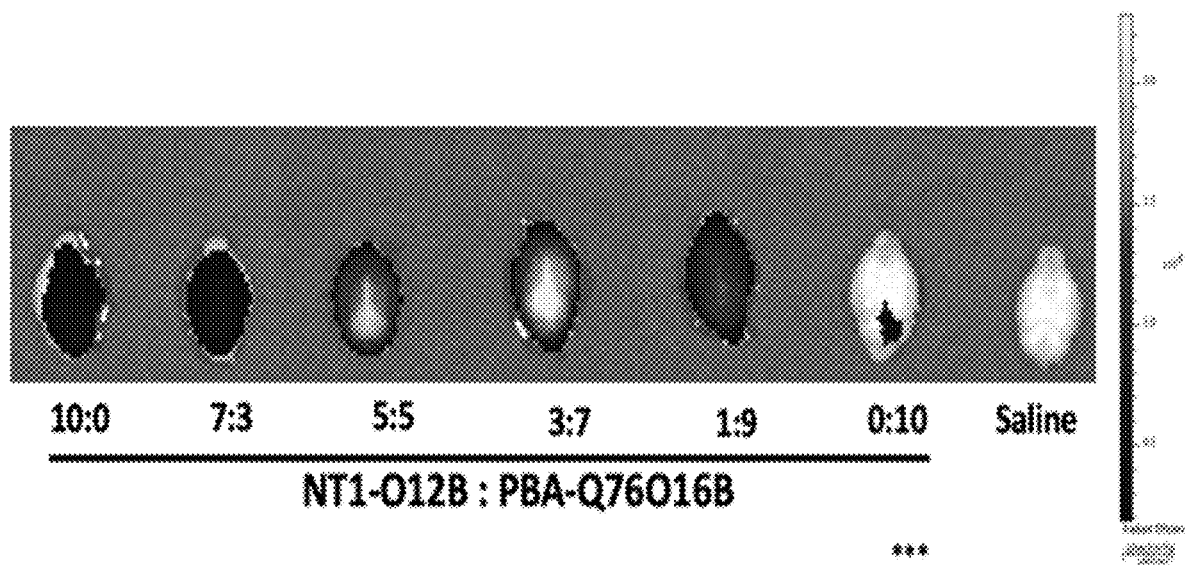
FIG. 2D are representative fluorescence images of the dissected mouse brain 1 h after one-time intravenous injection of 1 mg kg$^{-1}$ DiR-loaded NT1-O12B/PBA-Q76-O16B LNPs. The weight ratio of DiR in LNPs is 10%.
Figure 2E:
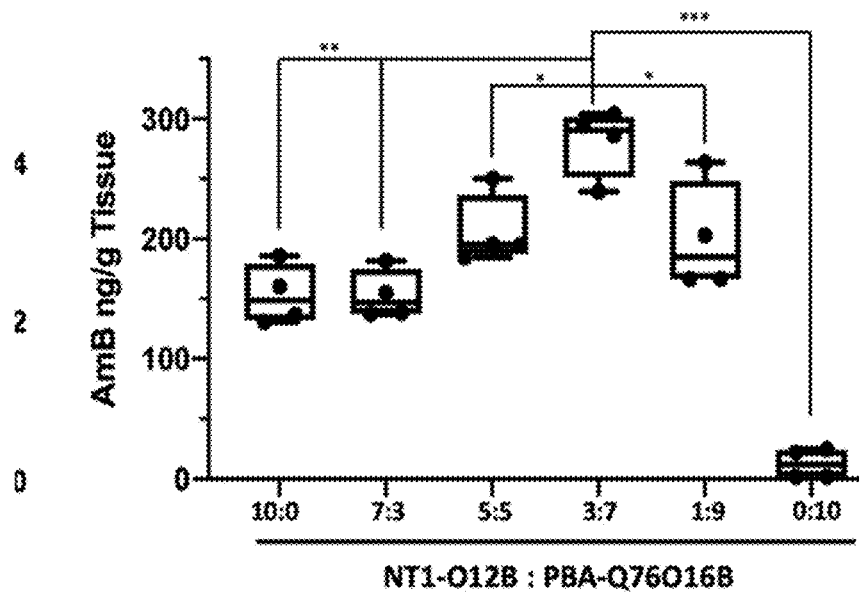
FIG. 2E is a graph depicting AmB concentration in brain tissues 24 hr after intravenous injection of 5 mg/kg AmB in various NT1-O12B/PBA-Q76-O16B LNPs LNP formulations measured using HPLC (n=4 per group). The mice were perfused with saline before dissected. One-way ANOVA, Sidak post hoc analysis, *p<0.05, **p<0.001 or \*\*\*p<0.0001. Graphical data are represented as box and whisker plots with individual points overlaid, where error bars represent maximum and minimum values and the boxed line represents the median.
Figure 11:
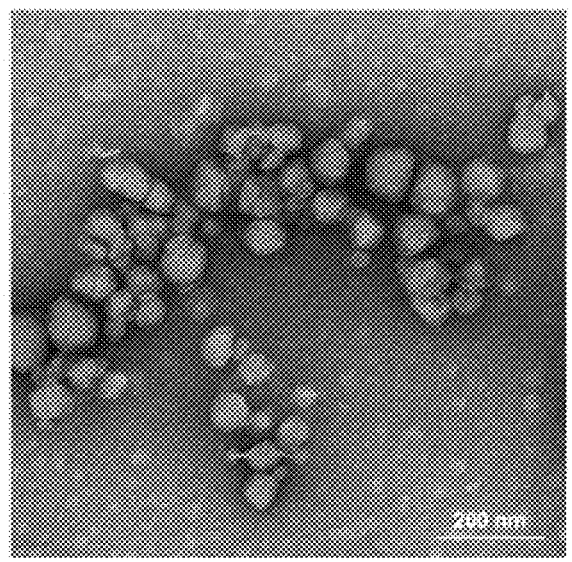
FIG. 11 is a TEM image of NT1-O12B/PBA-Q76016B-3/7-AmB complex, and a table that summarizes hydrodynamic sizes, polydispersity index, zeta potential, and DLC of AmB/NT-LNPs complex.
Figure 12:
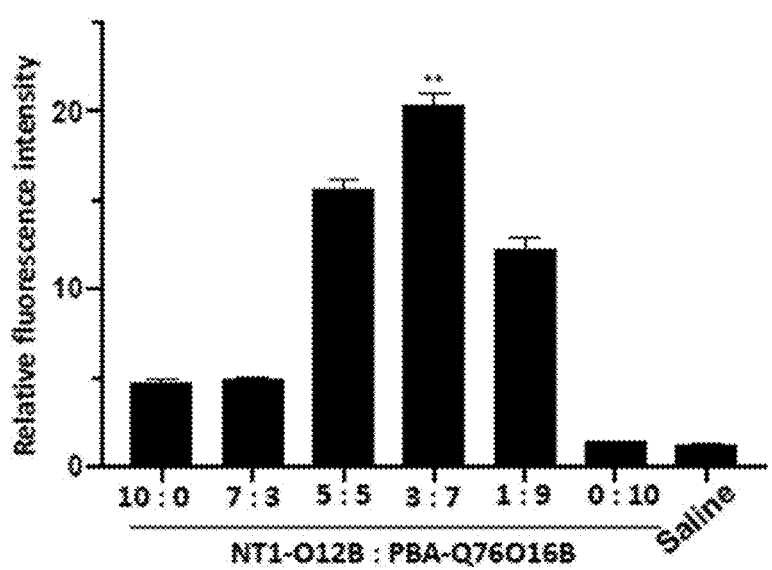
FIG. 12 is a graph that summarizes relative fluorescence intensity of the dissected brain tissue 1 h after one-time intravenous injection 1 mg kg-1 DiR-loaded NT1-O12B/PBA-Q76-O16B LNPs. The weight ratio of DiR in LNPs is 10%. **p<0.001. One-way ANOVA, Sidak post hoc analysis.
Figure 13:
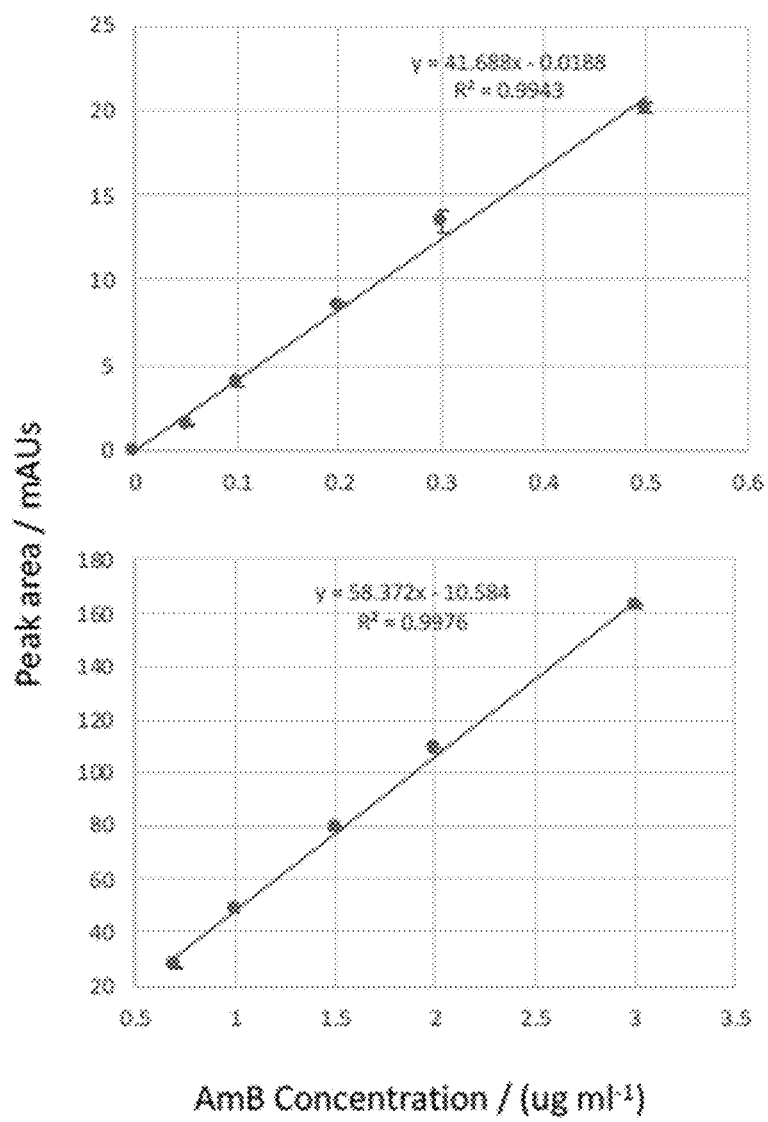
FIG. 13 is a calibration curve of AmB concentration dissolved in methanol ranging from 0.005 to 0.5 ug/mL (low concentration), or 0.007 to 3.0 ug/mL (high concentration) at 415 nm by HPLC.
Figure 14:
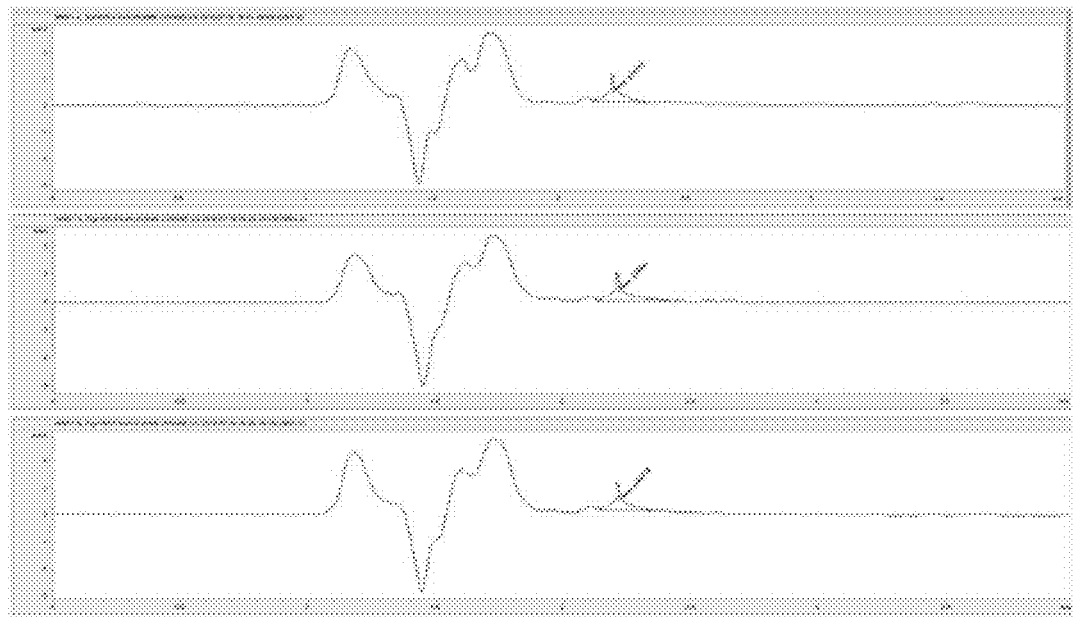
FIG. 14 is mAU-time graphs of AmB concentrations in brain tissues 24 h after intravenous treatment with NT1-O12B/PBA-Q76016-LNPs (ratio: 3/7)-AmB complex at a single dose of 5 mg AmB/kg by HPLC.
Figure 15:
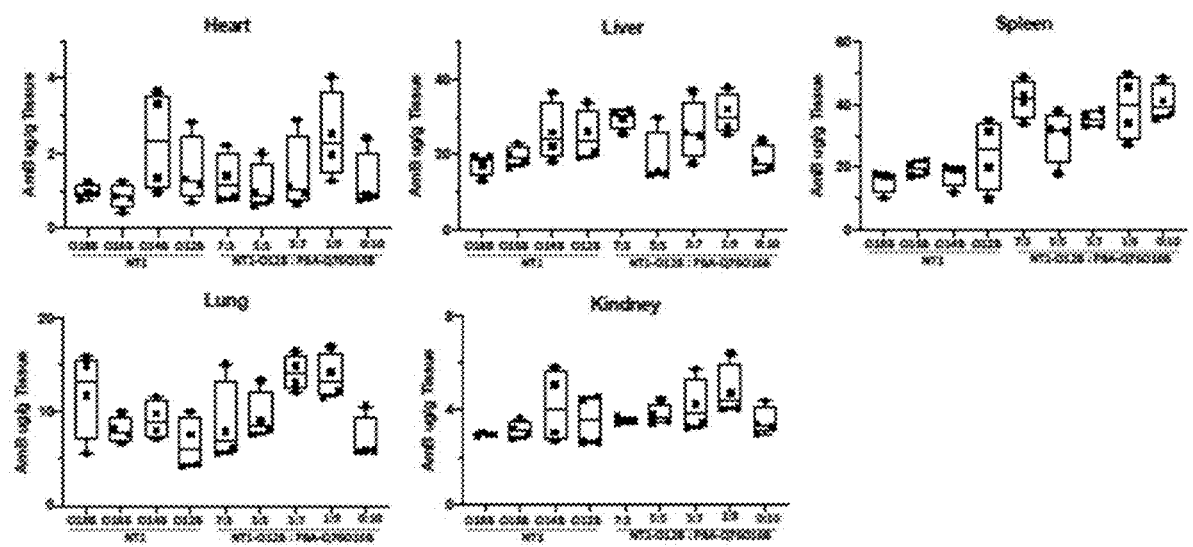
FIG. 15 are graphs depicting AmB concentrations in other organs 24 h after intravenous injection of 5 mg/kg AmB measured by HPLC.
Figure 16:
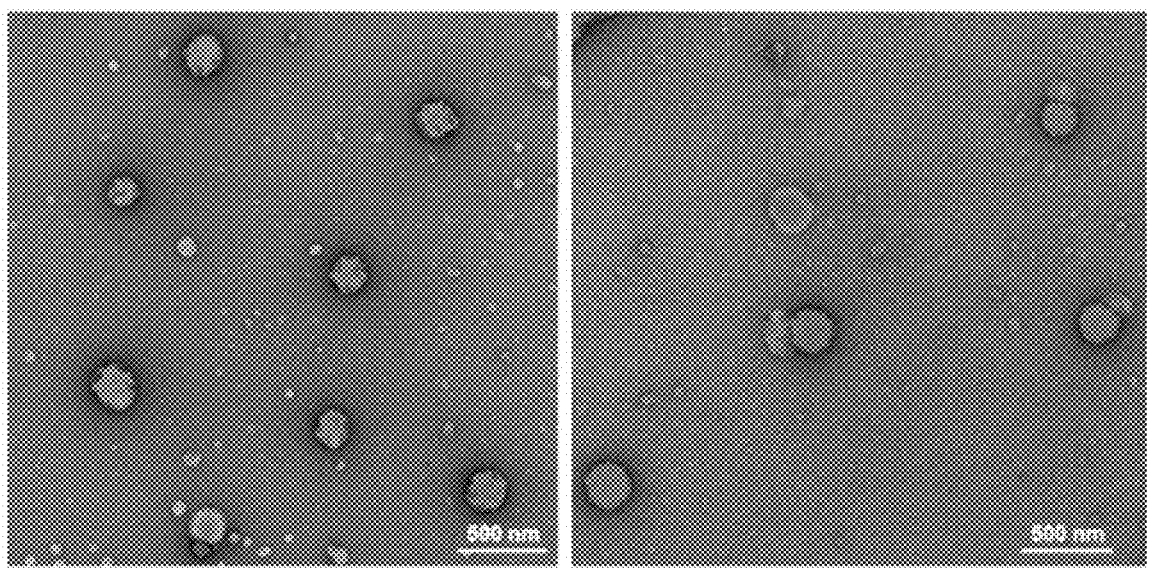
FIG. 16 is TEM images of blank and ASO loaded NT1-O14B/306-O12B-3 (ratio: 3/7) nanoparticles and a table of hydrodynamic sizes, polydispersity index, zeta potential.
Figure 17:
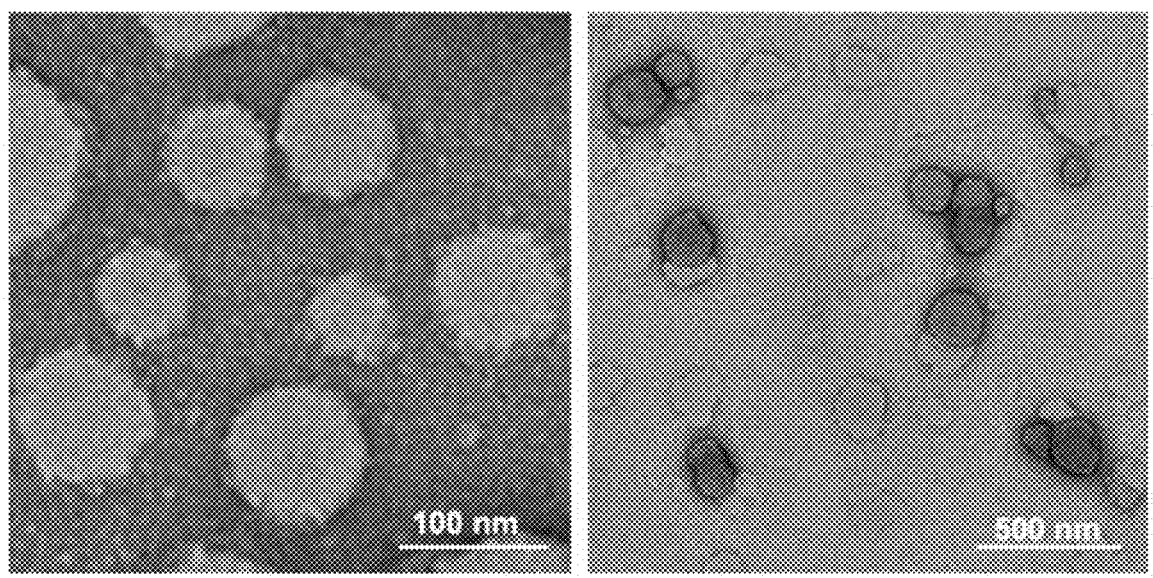
FIG. 17 are TEM images of blank and (−27)GFP-Cre loaded NT1-O14B/PBA-Q76016B (ratio: 3/7) nanoparticles and a table of hydrodynamic sizes, polydispersity index, zeta potential.

Here a new phenylboronic acid quaternized lipidoid was synthesized, PBA-Q76-O16B (FIG. 2A) for AmB encapsulation. NT1-O12B was chosen as the dopant for enhanced brain delivery since it showed the highest DiR fluorescence intensity (FIG. 1C) among all NT lipidoids. The AmB was formulated in the mixture of NT1-O12B and PBA-Q76-O16B, with the two lipidoids mixed at different weight ratios (7:3, 5:5, 3:7, 1:9, and pure PBA-Q76-O16B). As shown in FIG. 2B, the AmB encapsulates gradually became homogenous transparent yellow solution with the increasing percentage of PBA-Q76-O16B lipidoid in the formulations. The hydrodynamic sizes also decreased from 800 nm to 100 nm (FIG. 2C, FIG. 11). Using DiR as a cargo, we observed that lipidoids containing NT1-O12B and PBA-Q76-O16B at a 3:7 (w/w) ratio provided the strongest fluorescent signal in mouse brain when compared with all other lipid ratios (FIG. 2D). The fluorescent signal intensity at a 3:7 ratio was 4.5 folds higher than that of brain treated with DiR formulated in pure NT1-O12B (FIG. 12). The AmB delivery using the mixed lipids was further studied and determined the AmB concentration in the mice brain tissue 24 hr after intravenous injection of 5 mg/kg AmB per mouse. As shown in FIG. 2E, the amount of AmB detected in the brain increased as the doping ratio of PBA-Q76-O16B increased from 0% (i.e. pure NT1-O12B) to 70% (i.e. 3:7 ratio) and reached a highest concentration around 300 ng/g, which was about 2 folds higher than pure NT1-O12B. When the doping ratio increased further to 90% (i.e. 1:9), the AmB concentration was slightly lower, but was still higher than of that treated with AmB formulated in pure NT1-O12B. Thus, the results for AmB delivery closely matched the results for DiR delivery (FIGS. 2D and 2E). Interestingly, without doping with NT1-lipidoid, the AmB was nearly undetectable in the brain after intravenous injection of pure PBA-Q76-O16B/

AmB. These results showed the key role of NT1 lipidoids in facilitating the brain delivery, and the importance of finding the optimal doping ratio.

Delivery of Nucleic Acid Tau-ASOs into Mouse Brain for Gene Knockdown

The efficiency of the mixed lipidoid formulations for ASO delivery in vitro by delivering ASO targeting GFP mRNA to HEK cells stably expressing green fluorescent protein (GFP) (FIG. 3B) was evaluated. The NT1-O14B alone showed no GFP silencing effect (10:0 ratio in FIG. 3B), indicating that this lipidoid alone is not effective for delivering ASO intracellularly. However, GFP silencing was observed when the ASO was delivered using LNPs containing a mixture of NT1-O14B and 306-O12B-3. When the doping ratio of 306-O12B-3 was greater than 50% (i.e. 5:5 weight ratio or more in favor of 306-O12B-3), the GFP silencing in GFP-HEK cells was observed, silencing efficiency increasing as the 306-O12B-3 doping ratio increased. Scrambled ASO delivered by Lipofetamine 2000 (LPF 2K) showed no GFP silencing, indicating the GFP silencing was truly ASO sequence-specific.

Whether the mixed lipidoid formulation (NT1-O14B and 306-O12B-3) could deliver ASO to the brain and mediate the gene knockdown in vivo was then explored. Tau was chosen as a therapeutic target and designed ASO targeting tau mRNA, since ASO-mediated tau reduction has shown promising results in the treatment of Alzheimer's disease (AD) after the local injection of the Tau-ASO using an intracerebroventricular (ICV) pump.[31,32]

Figure 3A:
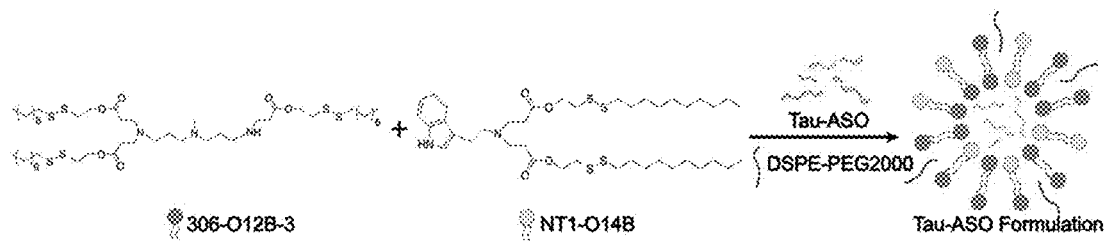
FIG. 3A shows chemical structures of 306-O12B-3, NT1-O14B, and schematic illustration of the doped NT-lipidoid Tau-ASO formulation for brain delivery.
Figure 3B:
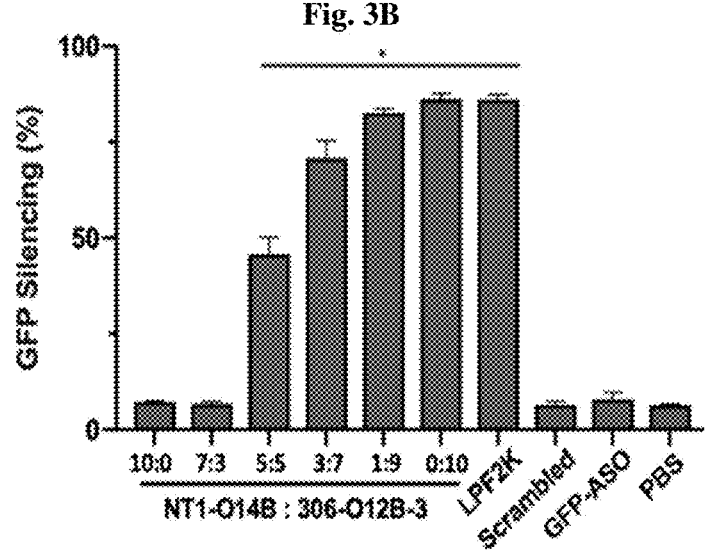
FIG. 3B is a graph depicting GFP silencing efficiency of HEK-GFP cells treated with or without ASO/NT-LNPs complexes. The NT1-O14B LNPs alone showed no silencing efficacy, while doping NT1-lipidoid into 306-O12B-3 LNPs led to successful gene silencing in vitro. *p<0.01 vs. all other samples in the same group.

The sequence of Tau-ASO was chosen according to the published literature[31] and was synthesized by IDT. Tau-ASO was supplied containing chemical modification with phosphorothioate groups between each nucleic acid and 2'-O-methoxyethyl in the 5 nucleotides on the 5'- and 3'-termini of ribose to improve efficacy. To formulate the ASO for intravenous injection, the ASO with the formulated LNP solution is mixed at a weight ratio of 1/15 (ASO to total lipids). Each mouse received five injections of 1 mg/kg ASO, with each injection spaced three days apart. The mice were sacrificed four days after the last injection, perfused and the brain tissues were harvested and homogenized to extract the total RNA. The total tau mRNA levels were analyzed by quantitative PCR. As shown in FIG. 3C, when ASO was delivered using either pure NT1-O14B or pure 306-O12B-3, no tau mRNA reduction in the brain tissues was detected. For the mixed lipidoid formulations, only NT1-O14B and 306-O12-3 with a w/w ratio of 5:5 and 3:7 displayed tau mRNA reduction in the brain. These two formulations resulted in ~25% and ~50% mRNA reduction, respectively. No tau mRNA silencing was observed in the mixed lipidoid formulations in other ratios (i.e. 7:3 and 1:9).

To confirm the ASO delivery resulted in functional knockdown of tau, we also checked the tau protein level of the ASO treated mice using ELISA (FIG. 3D). Comparing with the untreated group, mice treated with Tau-ASO formulated in NT1-O14B/306-O12B-3 (3:7 w/w) showed substantially reduced total tau protein level. Furthermore, scrambled Tau-ASO was delivered with the best-performing ratios (NT1-O14B/306-O12B-3 at 3:7 w/w) using the exact same method as that of functional ASO. As shown, no tau mRNA silencing effect nor tau protein reduction was detected, demonstrating the tau knockdown is specifically due to sequence-specific ASO silencing.

Delivery of GFP-Cre Fusion Protein for Gene Recombination in the Ai14 Mouse Brain GFP fused Cre recombinase was chosen as a model protein for the study, using the Ai14 model mouse line (FIG. 4A). The Ai14 mouse line contains a flox-stop-flox tdTomato construct. The successful intracellular delivery of Cre protein into the cells of Ai14 mouse leads to the gene recombination and turns on the tdTomato expression which can be directly visualized as red fluorescence signal without additional staining. Here, (−27)GFP-Cre protein was used. NT1-O14B LNPs doped with PBA-Q76-O16B was chosen, as these nanoparticles could successfully deliver (−27)GFP-Cre. The weight ratio of NT1-O14B and PBA-Q76-O16B was fixed at 3:7, based on the results observed from the AmB and ASO delivery. Lipid formulations were prepared using the approaches described for the formulation for ASO delivery. Briefly, the (−27)GFP-Cre protein was mixed with LNPs at a weight ratio of 1/4 and incubated the solution for 15 min at room temperature before intravenous injection. Mice were injected four times with a dose of 50 μg protein per injection. Five days after the last injection, the mice were sacrificed and brain tissues were collected, fixed, and dehydrated. Then the tissues were cryo-sectioned into m slices and counter-stained with DAPI for fluorescence imaging. As shown in FIG. 4B, strong tdTomato signals were observed in multiple regions of the brain, including cerebral cortex, hippocampus and cerebellum. In contrast, no tdTomato expression in the brain was observed for the mice injected with LNP formulations using either pure NT1-O14B (10:0) or pure PBA-Q76-O16B (0:10).

Delivery of Different Formulation of GFP-Cre Fusion Protein for Gene Recombination in the Ai14 Mouse Brain NT1-O14B was doped into various lipid nanoparticle formulations, including 306-O12B, PBA-Q76O16B, Dlin-MC3, to investigate the doped LNP formulation for Cre mRNA delivery into the brain of Ai14 mouse through i.v. injection. The weight ratio of NT1-O14B and the other ionizable lipid (e.g. 306-O12B, PBA-Q76O16B, Dlin-MC3) is 3:7. To formulate stable LNP, other co-lipids including (1,2-distearoyl-sn-glycero-3-phosphoethanolamine-N-[methoxy(polyethylene glycol)-2000] (DSPE-PEG2000)), cholesterol and DOPE were also included. mRNA encoding Cre recombinase was loaded into the LNP, and injected in Ai14 mice. The mice were sacrificed at a specific time point, and brain tissues were collected, fixed, and dehydrated. Then the tissues were cryo-sectioned into 15 μm slices and counter-stained with DAPI for fluorescence imaging. The tdTomato signals were observed in multiple regions of the brain, indicating the successful delivery of Cre mRNA into brain cells with such LNP formulation through systemic injection. The fluorescence images of section of Ai14 mouse brain were shows in FIGS. 19A-19N, FIGS. 20A-20B, and FIGS. 21A-21B. The NT1-O14B doped 306-O12B showed highest brain delivery comparing with that doped in PBA-076016B or Dlin-MC3 LNP.

REFERENCES CITED

1. Pardridge, W. M. Blood-brain barrier delivery. *Drug Discov. Today* 12, 54-61 (2007).
2. Barchet, T. M. & Amiji, M. M. Challenges and opportunities in CNS delivery of therapeutics for neurodegenerative diseases. *Expert Opin. Drug Del.* 6, 211-225 (2009).
3. Collins, P. Y. et al. Grand challenges in global mental health. *Nature* 475, 27-30 (2011).
4. Obermeier, B., Daneman, R. & Ransohoff, R. M. Development, maintenance and disruption of the blood-brain barrier. *Nat. Med.* 19, 1584-1596 (2013).
5. Khorkova, O. & Wahlestedt, C. Oligonucleotide therapies for disorders of the nervous system. *Nat. Biotechnol.* 35, 249-263 (2017).

6. Patel, M. M. & Patel, B. M. Crossing the blood-brain barrier: recent advances in drug delivery to the brain. *CNS Drugs* 31, 109-133 (2017).
7. Dong, X. Current strategies for brain drug delivery. *Theranostics* 8, 1481-1493 (2018).
8. Fung, L. K., Shin, M., Tyler, B., Brem, H. & Saltzman, W. M. Chemotherapeutic drugs released from polymers: distribution of 1, 3-bis (2-chloroethyl)-1-nitrosourea in the rat brain. *Pharm. Res.* 13, 671-682 (1996).
9. Rubenstein, J. L. et al. Phase I study of intraventricular administration of rituximab in patients with recurrent CNS and intraocular lymphoma. *J. Clin. Oncol.* 25, 1350-1356 (2007).
10. Lu, C.-T. et al. Current approaches to enhance CNS delivery of drugs across the brain barriers. *Int. J. Nanomedicine* 9, 2241-2257 (2014).
11. Villringer, K. et al. DCE-MRI blood-brain barrier assessment in acute ischemic stroke. *Neurology* 88, 433-440 (2017).
12. Fu, H. & McCarty, D. M. Crossing the blood-brain-barrier with viral vectors. *Curr. Opin. Virol.* 21, 87-92 (2016).
13. Ha, D., Yang, N. & Nadithe, V. Exosomes as therapeutic drug carriers and delivery vehicles across biological membranes: current perspectives and future challenges. *Acta Pharm. Sin. B* 6, 287-296 (2016).
14. Pardridge, W. M. Drug and gene targeting to the brain with molecular Trojan horses. *Nat. Rev. Drug Discov.* 1, 131-139 (2002).
15. Zhou, Y., Peng, Z., Seven, E. S. & Leblanc, R. M. Crossing the blood-brain barrier with nanoparticles. *J. Control. Release* 270, 290-303 (2018).
16. Mingozzi, F. & High, K. A. Immune responses to AAV vectors: overcoming barriers to successful gene therapy. *Blood* 122, 23-36 (2013).
17. Pardridge, W. M. Delivery of biologics across the blood-brain barrier with molecular Trojan horse technology. *BioDrugs* 31, 503-519 (2017).
18. Blanco, E., Shen, H. & Ferrari, M. Principles of nanoparticle design for overcoming biological barriers to drug delivery. *Nat. Biotechnol.* 33, 941-951 (2015).
19. Wen, J. et al. Sustained delivery and molecular targeting of a therapeutic monoclonal antibody to metastases in the central nervous system of mice. *Nat. Biomed. Eng.* 3, 706-716 (2019).
20. Snowman, A. M. & Snyder, S. H. Cetirizine: actions on neurotransmitter receptors. *J. Allergy Clin. Immunol.* 86, 1025-1028 (1990).
21. Carbonaro, T. M. & Gatch, M. B. Neuropharmacology of N, N-dimethyltryptamine. *Brain Res. Bull.* 126, 74-88 (2016).
22. Wang, M. et al. Efficient delivery of genome-editing proteins using bioreducible lipid nanoparticles. *Proc. Natl. Acad. Sci. U.S.A.* 113, 2868-2873 (2016).
23. Chang, J. et al. Integrating Combinatorial Lipid Nanoparticle and Chemically Modified Protein for Intracellular Delivery and Genome Editing. *Acc. Chem. Res.* 52, 665-675 (2018).
24. Wang, M., Alberti, K., Sun, S., Arellano, C. L. & Xu, Q. Combinatorially designed lipid-like nanoparticles for intracellular delivery of cytotoxic protein for cancer therapy. *Angew. Chem. Int. Ed.* 53, 2893-2898 (2014).
25. Ostrosky-Zeichner, L., Marr, K. A., Rex, J. H. & Cohen, S. H. Amphotericin B: time for a new "gold standard". *Clin. Infect. Dis.* 37, 415-425 (2003).
26. Xu, N. et al. Efficacy of intravenous amphotericin B-polybutylcyanoacrylate nanoparticles against cryptococcal meningitis in mice. *Int. J. Nanomedicine* 6, 905-913 (2011).
27. Liu, F. et al. In vitro and in vivo study of an Amphotericin B formulation with quaternized bioreducible lipidoids. *ACS Biomater. Sci. Eng.* 6, 1064-1073 (2020).
28. Rinaldi, C. & Wood, M. J. Antisense oligonucleotides: the next frontier for treatment of neurological disorders. *Nat. Rev. Neurol.* 14, 9-21 (2018).
29. Talbot, K. & Wood, M. J. Wrangling RNA: Antisense oligonucleotides for neurological disorders. *Sci. Transl. Med.* 11, eaay2069 (2019).
30. Yang, L. et al. Efficient delivery of antisense oligonucleotides using bioreducible lipid nanoparticles in vitro and in vivo. *Mol. Ther. Nucleic Acids* (2020). https://doi.org/10.1016/j.omtn.2020.01.018
31. DeVos, S. L. et al. Antisense reduction of tau in adult mice protects against seizures. *J. Neurosci.* 33, 12887-12897 (2013).
32. DeVos, S. L. et al. Tau reduction prevents neuronal loss and reverses pathological tau deposition and seeding in mice with tauopathy. *Sci. Transl. Med.* 9, eaag0481 (2017).

INCORPORATION BY REFERENCE

All U.S. and PCT patent publications and U.S. patents mentioned herein are hereby incorporated by reference in their entirety as if each individual patent publication or patent was specifically and individually indicated to be incorporated by reference. In case of conflict, the present application, including any definitions herein, will control.

OTHER EMBODIMENTS

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

I claim:

1. A compound of formula I:

or a pharmaceutically acceptable salt thereof, wherein Y is

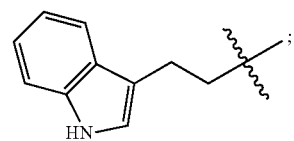 [SMILES: *CCc1c[nH]c2ccccc12]

W is —NR$^{20}$;
R$^{20}$ is R$^{Lipid}$; and
each instance of R$^{Lipid}$ is independently of the structure:

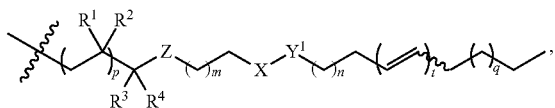

wherein:
  each instance of R$^1$ and R$^2$ is independently —H, —OH, —NHR$^{30}$, or —SH;
  R$^3$ and R$^4$ are both —H; or R$^3$ and R$^4$ are taken together to form an oxo (=O) group;
  Z is —CH$_2$—, —O—, —NR$^{30}$—, or —S—;
  X and Y$^1$ are independently —CH$_2$—, —NR$^{30}$—, —O—, —S—, or —Se—;
  m is an integer selected from 1-3;
  n is an integer selected from 1-14;
  p is 0 or 1;
  q is an integer selected from 1-10;
  t is 0 or 1; and
  R$^{30}$ is —H, C$_{1-6}$ alkyl, C$_{2-6}$ alkenyl, or C$_{2-6}$ alkynyl.

2. The compound of claim 1, wherein, in at least one instance of R$^{Lipid}$, R$^1$ and R$^2$ are —H, R$^3$ and R$^4$ are taken together to form an oxo (=O) group, and Z is O.

3. The compound of claim 1, wherein, in at least one instance of R$^{Lipid}$, m is 1.

4. The compound of claim 1, wherein, in at least one instance of R$^{Lipid}$, p is 1.

5. The compound of claim 1, wherein, in at least one instance of R$^{Lipid}$, q is an integer selected from 2-8.

6. The compound of claim 1, wherein, in at least one instance of R$^{Lipid}$, t is 0.

7. The compound of claim 1, selected from the group consisting of:

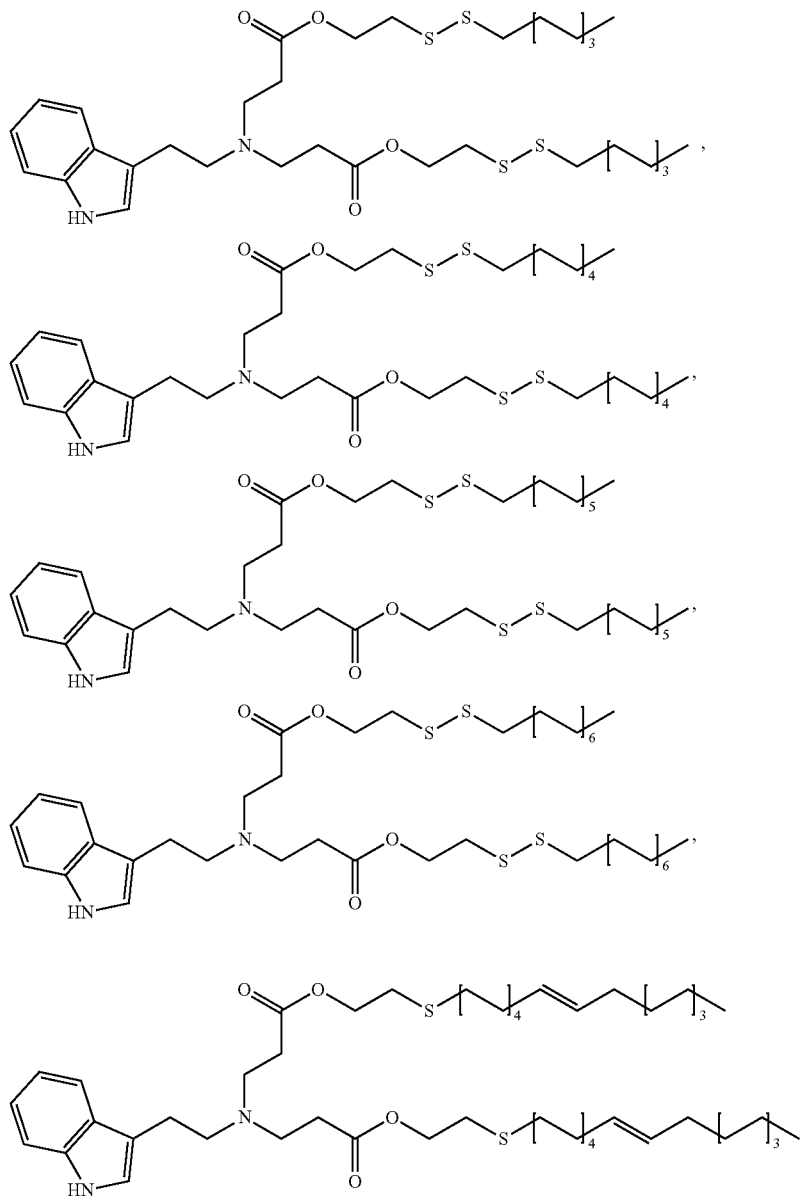

-continued

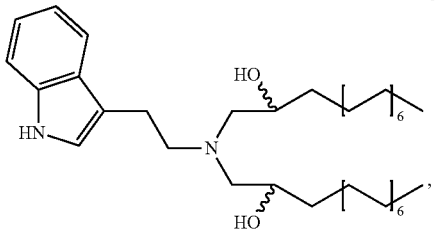 and 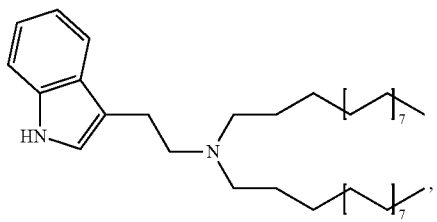, or a pharmaceutically acceptable salt thereof.

8. A lipidoid composition, comprising a compound of claim 1.

9. The lipidoid composition of claim 8, further comprising a protein.

10. The lipidoid composition of claim 9, wherein the protein is GFP-Cre.

11. The lipidoid composition of claim 8, further comprising a nucleic acid.

12. The lipidoid composition of claim 11, wherein the nucleic acid is Tau-ASO.

13. The lipidoid composition of claim 8, further comprising a small molecule, wherein the small molecule is an antifungal agent or a chemotherapeutic agent.

14. The lipidoid composition of claim 13, wherein the small molecule is selected from the group consisting of bortezomib, imatinib, gefitinib, erlotinib, afatinib, osimertinib, dacomitinib, daunorubicin hydrochloride, cytarabine, fluorouracil, irinotecan hydrochloride, vincristine sulfate, methotrexate, paclitaxel, vincristine sulfate, epirubicin, docetaxel, cyclophosphamide, carboplatin, lenalidomide, ibrutinib, abiraterone acetate, enzalutamide, pemetrexed, palbociclib, nilotinib, everolimus, ruxolitinib, epirubicin, pirirubicin, idarubicin, valrubicin, amrubicin, bleomycin, phleomycin, dactinomycin, mithramycin, streptozotecin, pentostatin, mitosanes, enediynes, glycosides, macrolide lactones, ixabepilone, pentostatin, salinosporamide A, vinblastine, vincristine, etoposide, teniposide, vinorelbine, docetaxel, camptothecin, hycamtin, pederin, theopederins, annamides, trabectedin, aplidine, and ecteinascidin 743 (ET743).

15. The lipidoid composition of claim 8, wherein the lipidoid composition has a particle size of about 25 nm to about 1000 nm.

16. A pharmaceutical composition, comprising a lipidoid composition of claim 8; and a pharmaceutically acceptable carrier or excipient.

* * * * *